US 7,285,138 B2

(12) United States Patent
Greaves et al.

(10) Patent No.: US 7,285,138 B2
(45) Date of Patent: Oct. 23, 2007

(54) CATIONIC DIAZO COMPOUND, COMPOSITIONS COMPRISING AT LEAST ONE CATIONIC DIAZO COMPOUND AS A DIRECT DYE, A PROCESS FOR DYEING KERATIN FIBERS AND DEVICE THEREFORE

(75) Inventors: Andrew Greaves, Montevrain (FR); Hervé David, Joinville le Pont (FR)

(73) Assignee: L'Oreal, S.A., Paris (FR)

( * ) Notice: Subject to any disclaimer, the term of this patent is extended or adjusted under 35 U.S.C. 154(b) by 302 days.

(21) Appl. No.: 11/159,154

(22) Filed: Jun. 23, 2005

(65) Prior Publication Data

US 2006/0021162 A1    Feb. 2, 2006

Related U.S. Application Data

(60) Provisional application No. 60/588,041, filed on Jul. 15, 2004.

(30) Foreign Application Priority Data

Jun. 23, 2004   (FR)   .................................. 04 06871

(51) Int. Cl.
A61K 7/13   (2006.01)

(52) U.S. Cl. .................. 8/405; 8/406; 8/407; 8/408; 8/410; 8/437; 8/571; 8/573; 8/574; 548/318.1; 548/321.1; 548/400; 546/184; 546/249; 534/608

(58) Field of Classification Search .................... 8/405, 8/406, 407, 408, 410, 437, 571, 573, 574; 548/318.1, 400; 546/184, 249; 534/608
See application file for complete search history.

(56) References Cited

U.S. PATENT DOCUMENTS

| | | |
|---|---|---|
| 3,151,106 A | 9/1964 | Tsang et al. |
| 4,003,699 A | 1/1977 | Rose et al. |
| RE30,199 E | 1/1980 | Rose et al. |
| 4,563,191 A | 1/1986 | Hähnke et al. |
| 4,823,985 A | 4/1989 | Grollier et al. |
| 5,061,289 A | 10/1991 | Clausen et al. |
| 5,380,340 A | 1/1995 | Neunhoeffer et al. |
| 5,534,267 A | 7/1996 | Neunhoeffer et al. |
| 5,663,366 A | 9/1997 | Neunhoeffer et al. |
| 5,708,151 A | 1/1998 | Möckli |
| 5,766,576 A | 6/1998 | Löwe et al. |
| 5,792,221 A | 8/1998 | Lagrange et al. |
| 5,852,179 A | 12/1998 | Dado |
| 6,099,593 A | 8/2000 | Terranova et al. |
| 6,284,003 B1 | 9/2001 | Rose et al. |
| 6,645,258 B2 | 11/2003 | Vidal et al. |
| 6,884,265 B2 | 4/2005 | Vidal et al. |
| 2004/0244124 A1 | 12/2004 | Plos et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 044 059 | 1/1982 |
| EP | 0 714 954 | 6/1996 |
| EP | 0 770 375 | 5/1997 |
| EP | 1 133 976 | 9/2001 |
| FR | 2 586 913 | 3/1987 |
| FR | 2 692 572 | 12/1993 |
| FR | 2 733 749 | 11/1996 |
| FR | 2 750 048 | 12/1997 |
| GB | 1026978 | 4/1966 |
| GB | 1153196 | 5/1969 |
| JP | 2-19576 | 1/1990 |
| JP | 5-163124 | 6/1993 |
| WO | WO94/08969 | 4/1994 |
| WO | WO94/08970 | 4/1994 |
| WO | WO95/01772 | 1/1995 |

(Continued)

OTHER PUBLICATIONS

STIC Search Report dated on May 10, 2007.*
Erwin Buncel and Sam-Rok Keum, "Studies of Azo and Azoxy Dyestuffs–16. Investigations of the Protonation and Tautomeric Equilibria of 4-(p'-Hydroxyphenylazo)pyridine and Related Substrates," Tetrahedron, vol. 39, No. 7, pp. 1091-1101 (1983).
Mohammed H. Habibi, "Efficient Catalytic Oxidation of Primary Aromatic Amines to Azo Derivatives by Manganese (III) Tetraphenylporphyrin," J. Chem. Research, Issue, 10, pp. 648-649 (1998).

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The present disclosure relates to a cationic diazo compound of formula (I):

Dye1-LK-Dye2 wherein Dye1 and Dye2 are such that the compound of formula (I) is not symmetrical, and are chosen from:

Dye1:

$$W_3-N=N-W_2-W_1 \qquad W_3-N=N-W'_2 | W'_1$$

Dye2:

$$W_4-N=N-W_5-W_6 \qquad W_4-N=N-W'_5 | W'_6$$

The disclosure also relates to dye compositions comprising compounds of formula (I) as direct dye, and further relates to a process for dyeing keratin fibers using the compositions disclosed herein and also to a multi-compartment device.

38 Claims, No Drawings

FOREIGN PATENT DOCUMENTS

| WO | WO95/15144 | 6/1995 |
|---|---|---|
| WO | WO96/15765 | 5/1996 |
| WO | WO 02/078596 A2 * | 10/2002 |
| WO | WO 02078596 | 10/2002 |
| WO | WO 02/100366 | 12/2002 |

OTHER PUBLICATIONS

Ikenna Onyido and Collins I. Ubochi, "Heteroaromatic Azo-Activated Nucleophilic Substitutions. The Reaction of 4-(p-Methoxyphenylazo)pyridinium Methiodine with Piperidine in Dimethyl Sulphoxide," Heterocycles, vol. 26, No. 2, pp. 313-317 (1987).

Xiao-Yang Wang et al., "The Preparation of Symmetrical Azobenzenes from Anilines by Phase Transfer Catalyzed Method," Synthetic Communications, vol. 29, No. 13, pp. 2271-2276 (1999).

Siegfried Hünig and Gert Köbrich, "Synthese von 1-substitulerten Pyridon-(4)-hydrazonen," Liebigs Ann. Chem., 617, pp. 180-202 (1958).

English language DERWENT abstract of EP 0 770 375 (1997).

English language DERWENT abstract JP 2-19576 (1990).

English language DERWENT abstract of JP 5-163124 (1993).

French Search Report dated Feb. 15, 2005, for FR 0406872 (French Priority Application for co-pending U.S. Appl. No. 11/159,267) Examiner Kirsch.

French Search Report dated Feb. 16, 2005, for FR 0406871 (French Priority Application for U.S. Appl. No. 11/159,154, the present application) Examiner Kirsch.

IFrench Search Report dated Feb. 16, 2005, for FR 0406870 (French Priority Application for co-pending U.S. Appl. No. 11/159,242) Examiner Kirsch.

French Search Report dated Feb. 16, 2005, for FR 0406869 (French Priority Application for co-pending U.S. Appl. No. 11/159,237) Examiner Kirsch.

Co-Pending U.S. Appl. No. 11/159,267, Title: Cationic Diazo Compounds Compositions Comprising Them as Direct Dyes, Process for Dyeing Keratin Fibers and Device Therefor, Inventors: Andrew Greaves et al. filed Jun. 23, 2005.

Co-Pending U.S. Appl. No. 11/159,242, Title: Cationic Diazo Compounds, Compositions Comprising Them as Direct Dyes Process for Dyeing Keratin Fibers and Device Therefor, Inventors: Andrew Greaves et al. filed Jun. 23, 2005.

Co-Pending U.S. Appl. No. 11/159,237, Title: Cationic Diazo Compounds Compositions Comprising Them as Direct Dye, Process for Dyeing Keratin Fibers and Device Therefor, Inventors: Andrew Greaves et al. filed Jun. 23, 2005.

* cited by examiner

CATIONIC DIAZO COMPOUND, COMPOSITIONS COMPRISING AT LEAST ONE CATIONIC DIAZO COMPOUND AS A DIRECT DYE, A PROCESS FOR DYEING KERATIN FIBERS AND DEVICE THEREFORE

This application claims benefit of U.S. Provisional Application No. 60/588,041, filed Jul. 15, 2004, the contents of which are incorporated herein by reference.

This application also claims benefit of priority under 35 U.S.C. § 119 to French Patent Application No. 04 06871, filed Jun. 23, 2004, the contents of which are also incorporated by reference.

The present disclosure relates to a cationic diazo compound, to dye compositions comprising at least one cationic diazo compound as direct dye in a medium that is suitable for dyeing keratin fibers, and also to a process for dyeing keratin fibers using at least one composition comprising at least one cationic diazo compound and a multi-compartment device.

It is known practice to dye keratin fibers, for example, human keratin fibers such as the hair, with dye compositions comprising direct dyes. These compounds are colored and coloring molecules with affinity for the fibers. It is known practice, for example, to use direct dyes of the nitrobenzene type, anthraquinone dyes, nitropyridines and dyes of the azo, xanthene, acridine, azine or triarylmethane type.

These dyes are usually applied to the fibers, optionally in the presence of an oxidizing agent, if it is desired, to obtain simultaneous lightening of the fibers. Once the leave-in time has elapsed, the fibers are rinsed, optionally washed and dried.

The colorations resulting from the use of direct dyes are temporary or semi-permanent colorations since the nature of the interactions that bind the direct dyes to the keratin fiber, and their desorption from the surface and/or the core of the fiber, are responsible for their poor dyeing power and their poor relative resistance to washing or to perspiration.

An additional difficulty also arises, associated with the fact that in order to obtain a desired color, it is necessary in most if not all cases to mix together several dyes. However, each dye does not have the same affinity for the fibers, which is reflected either by heterogeneous colorations or by changes in color over time, for example after washing the fibers at least one time, exposure to sunlight, etc.

Disclosed herein in one embodiment are direct dyes that do not have the drawbacks of the existing direct dyes.

Disclosed herein in one embodiment are direct dyes with which varied shades may be obtained without the problem of changes in color over time.

Also, disclosed herein in one embodiment is a cationic diazo compound of formula (I):

Dye1-LK-Dye2 (I)

or the addition salts thereof with an acid, the electrical neutrality of the compounds is ensured by at least one cosmetically acceptable anion An, wherein:

Dye1 and Dye2 are such that the compound of formula (I) is not symmetrical, and are chosen from:

Dye1:

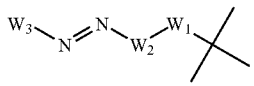 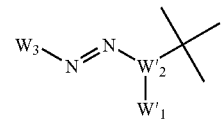

Dye2:

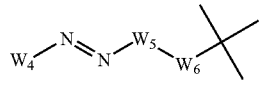 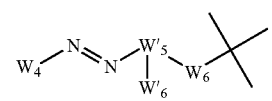

wherein:

$W_1$ and $W_6$, which may be identical or different, are each chosen from $-NR_1-$ and $-O-$, wherein R1 is chosen from a hydrogen atom, and saturated and unsaturated, aromatic and non-aromatic, optionally substituted $C_1-C_{20}$, for example, $C_1-C_{16}$, hydrocarbon-based chains, which may form at least one optionally substituted 3- to 7-membered carbon-based ring, optionally interrupted with at least one hetero atom or with at least one group bearing at least one hetero atom, for example, chosen from oxygen and nitrogen;

wherein $R_1$ may form with all or part of the group LK and with the nitrogen atom to which each is attached at least one cationic and non-cationic, saturated and unsaturated, aromatic and non-aromatic, optionally substituted 5- to 7-membered heterocycle;

$W'_1$ and $W'_6$, which may be identical or different, are each chosen from group $-NR'_1R'_2$ or $-OR'_3$, wherein $R'_1$, $R'_2$ and $R'_3$, which may be identical or different, are each chosen from a hydrogen atom and saturated and unsaturated, aromatic and non-aromatic, optionally substituted $C_1-C_{20}$, for example, $C_1-C_{16}$, hydrocarbon-based chains, which may form at least one optionally substituted 3- to 7-membered carbon-based ring, optionally interrupted with at least one hetero atom or with at least one group bearing at least one hetero atom, for example, chosen from oxygen and nitrogen; $R'_1$ and $R'_2$ optionally forming, with the nitrogen atom to which they are attached, an optionally substituted 5- or 7-membered heterocycle optionally comprising another nitrogen or non-nitrogen hetero atom;

wherein $R'_1$, $R'_2$ or $R'_3$ may form, with all or part of the group LK and with the nitrogen or oxygen atom to which each is attached, cationic and non-cationic, saturated and unsaturated, aromatic and non-aromatic, optionally substituted 5- to 7-membered heterocycles;

$W_2$, $W_5$, $W'_2$ and $W'_5$, which may be identical or different, are each chosen from:

(a)

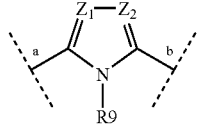

(b)

-continued

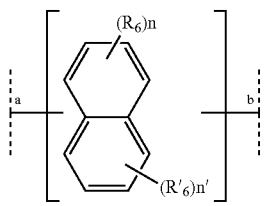

(c)

wherein:
X$_1$ is chosen from a nitrogen atom or CR$_7$;
X$_2$ is chosen from a nitrogen atom or CR$_8$;
Z$_1$ is chosen from a nitrogen atom or CR$_{10}$;
Z$_2$ is chosen from a nitrogen atom or CR$_{11}$;
R$_4$, R$_5$, R$_6$, R'$_6$, R$_7$, R$_8$, R$_{10}$ and R$_{11}$, which may be identical or different, are chosen from:
  a hydrogen atom
    linear and branched, saturated and unsaturated, aromatic and non-aromatic, optionally substituted C$_1$-C$_{16}$ hydrocarbon-based chain, which may form at least one optionally substituted 3- to 6-membered carbon-based rings, optionally interrupted with at least one hetero atom or with at least one group bearing at least one hetero atom, for example, chosen from oxygen and nitrogen;
  a hydroxyl group,
  a C$_1$-C$_4$ alkoxy group, a C$_2$-C$_4$ (poly)hydroxyalkoxy group; an alkoxycarbonyl group (RO—CO—) wherein R is chosen from a C$_1$-C$_4$ alkyl radical, and an alkylcarbonyloxy radical (RCO—O—) wherein R is chosen from a C$_1$-C$_4$ alkyl radical;
  an amino group, an amino group substituted with at least one C$_1$-C$_4$ alkyl radical, which may be identical or different, optionally bearing at least one hydroxyl group, the two alkyl radicals optionally forming, with the nitrogen atom to which they are attached, a 5- or 6-membered heterocycle optionally bearing another nitrogen or non-nitrogen hetero atom; an alkylcarbonylamino group (RCO—NR—) wherein R, which may be identical or different, are each chosen from C$_1$-C$_4$ alkyl radicals; a carbamoyl group ((R)$_2$N—CO) wherein R, which may be identical or different, are chosen from, a hydrogen atom and a C$_1$-C$_4$ alkyl radical; a ureido group (N(R)$_2$—CO—NR'—) wherein R and R', which may be identical or different, are each chosen from a hydrogen atom and a C$_1$-C$_4$ alkyl radical; a sulfonamide group ((R)$_2$N—SO$_2$—) wherein R, which may be identical or different, are each chosen from a hydrogen atom and a C$_1$-C$_4$ alkyl radical; an alkylsulfonylamino group (RSO$_2$—NR'—) wherein R and R', which may be identical or different, are each chosen from a hydrogen atom and a C$_1$-C$_4$ alkyl radical; a guanidinium group ((R')$_2$N—C(=NH$_2^+$)—NR—) wherein R and R', which may be identical or different, are each chosen from a hydrogen atom and a C$_1$-C$_4$ alkyl radical;
  a nitro group; a cyano group; a halogen atom, for example, chlorine or fluorine;
R$_4$, R$_5$, R$_6$, R'$_6$, R$_7$, R$_8$, R$_{10}$ and R$_{11}$, which may be identical or different, may optionally form, with all or some of the groups W'$_1$ or W'$_6$, a saturated and unsaturated, aromatic and non-aromatic, optionally substituted 5- to 7-membered heterocycles;
a bond from W'$_2$ to W'$_1$ or to the group LK, or from W'$_5$ to W'$_6$ or to the group LK;
a is the bond from W$_2$, W$_5$, W'$_2$ or W'$_5$ to the azo group —N=N—;
b is the bond from W$_2$ to W$_1$, from W$_5$ to W$_6$, from W'$_2$ to W'$_1$ or to the group LK, or from W'$_5$ to W'$_6$ or to the group LK;
R$_9$ is chosen from:
  a hydrogen atom,
  linear and branched, saturated and unsaturated, aromatic and non-aromatic, optionally substituted C$_1$-C$_{16}$ hydrocarbon-based chain, which may form at least one optionally substituted 3- to 7-membered carbon-based ring,
n and n' are chosen from integers and their sum is less than or equal to 6;
W$_3$ and W$_4$, which may be identical or different, are each chosen from cationic heteroaromatic radicals chosen from:

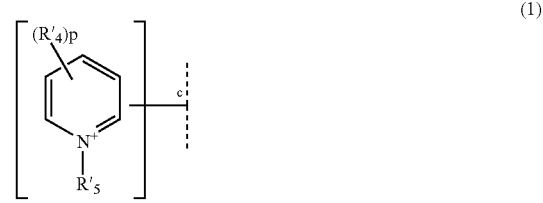

(1)

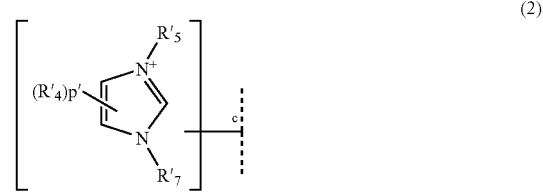

(2)

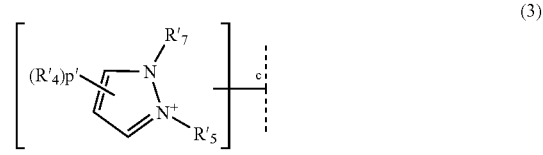

(3)

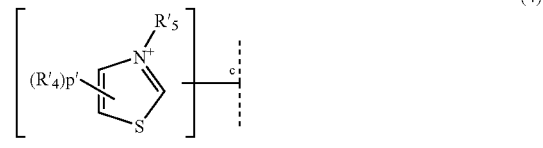

(4)

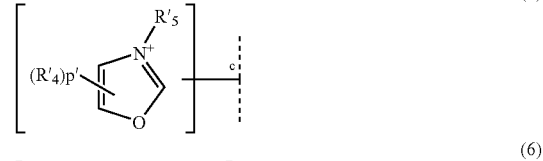

(5)

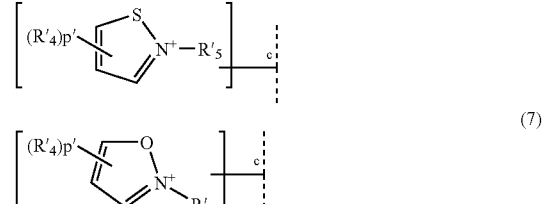

(6)

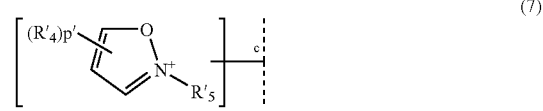

(7)

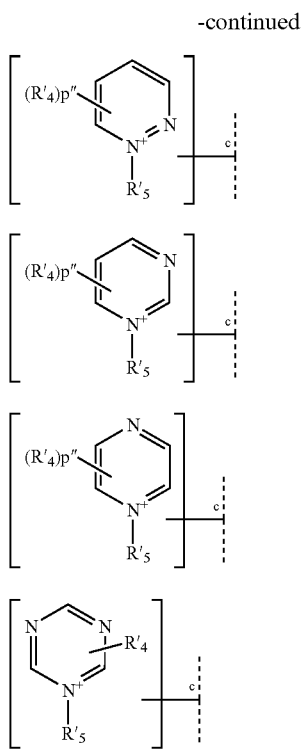

wherein R'₄, which may be identical or different, are chosen from:

linear and branched, saturated and unsaturated, aromatic and non-aromatic, optionally substituted $C_1$-$C_{16}$ hydrocarbon-based chains, which may form at least one 3- to 6-membered carbon-based ring, optionally interrupted with at least one hetero atom or with at least one group bearing at least one hetero atom, for example, chosen from oxygen and nitrogen;

a hydroxyl group, a $C_1$-$C_4$ alkoxy group, a $C_2$-$C_4$ (poly)hydroxyalkoxy group; an alkoxycarbonyl group (RO—CO—) wherein R is chosen from a $C_1$-$C_4$ alkyl radical, and an alkylcarbonyloxy radical (RCO—O—) wherein R is chosen from a $C_1$-$C_4$ alkyl radical;

an amino group, an amino group substituted with at least one $C_1$-$C_4$ alkyl radical, which may be identical or different, optionally bearing at least one hydroxyl group, the two alkyl radicals optionally forming, with the nitrogen atom to which they are attached, a 5- or 6-membered heterocycle optionally bearing another nitrogen or non-nitrogen hetero atom; an alkylcarbonylamino group (RCO—NR'—) wherein R is chosen from a $C_1$-$C_4$ alkyl radical and R' is chosen from a hydrogen and a $C_1$-$C_4$ alkyl radical; a carbamoyl group ((R)₂N—CO—) wherein R, which may be identical or different, are chosen from a hydrogen atom and a $C_1$-$C_4$ alkyl radical; a ureido group (N(R)₂—CO—NR'—) wherein R and R', which may be identical or different, are each chosen from a hydrogen atom arid a $C_1$-$C_4$ alkyl radical; a sulfonamide group ((R)₂N—SO₂—) wherein R, which may be identical or different, are each chosen from a hydrogen atom and a $C_1$-$C_4$ alkyl radical; an alkylsulfonylamino group (RSO₂—NR'—) wherein R and R', which may be identical or different, are each chosen from a hydrogen atom and a $C_1$-$C_4$ alkyl radical; a guanidinium group ((R')₂N—C(=NH₂⁺)—NR—) wherein R and R', which may be identical or different, are each chosen from a hydrogen atom and a $C_1$-$C_4$ alkyl radical;

a nitro group; a cyano group; a halogen atom, for example, chlorine or fluorine;

wherein two radicals R'₄ borne by two adjacent carbon atoms of a main ring may optionally form an aromatic or non-aromatic, 5- or 6-membered secondary-ring, optionally substituted with at least one group chosen from a hydrogen atom; hydroxyl groups; $C_1$-$C_4$ alkyl radicals; $C_1$-$C_4$ alkoxy radicals; $C_2$-$C_4$ (poly)hydroxyalkoxy radicals; amino radicals; amino radicals substituted with at least one $C_1$-$C_4$ alkyl radicals, which may be identical or different, optionally bearing at least one hydroxyl group; for example, the secondary ring is a 6-membered aromatic ring optionally substituted as disclosed above;

R'₅ is chosen from linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom, for example, chosen from oxygen, nitrogen and sulfur; wherein R'₅ is such that the atom directly linked to the quaternized nitrogen atom is a carbon atom;

R'₇ is chosen from an optionally substituted $C_1$-$C_4$ alkyl radical; an optionally substituted phenyl radical; and an optionally substituted benzyl radical;

the bond c links the cationic radical defined by formulae (1) to (11) to the azo group; wherein said bond may be on the main or secondary ring; for example, the bond c with the azo group is on the main ring;

p is an number ranging from 0 to 4, p' is an number ranging from 0 to 2 and p" is an number ranging from 0 to 3;

wherein, if the main ring does not bear the maximum number of substituents, then the unsubstituted position(s) bear(s) a nitrogen atom;

LK is chosen from saturated and unsaturated, linear and branched, cyclic and non-cyclic, aromatic and non-aromatic, optionally substituted $C_2$-$C_{40}$, for example, $C_2$-$C_{20}$ hydrocarbon-based chains, bearing at least one cationic charge, optionally interrupted with at least one hetero atom or group comprising at least one hetero atom, for example, oxygen or nitrogen;

wherein, LK may end with a hetero atom or group bearing at least one hetero atom, for example, oxygen or nitrogen, if LK is linked to W'₂ or W'₅; and wherein LK may end with a group bearing at least one hetero atom chosen from —CO— and —SO₂— if LK is linked to W₆ or W₁;

Another embodiment is a dye compositions comprising, in a medium that is suitable for dyeing keratin fibers, at least one compound of formula (I):

Dye1-LK-Dye2 (I)

or the addition salts thereof with an acid, the electrical neutrality of the compounds is ensured by at least one cosmetically acceptable anion An, wherein Dye1, LK and Dye2 are as defined above.

Another embodiment is a process for dyeing keratin fibers comprising placing at least one composition comprising, in a medium that is suitable for dyeing keratin fibers, at least one compound of formula (I):

$$\text{Dye1-LK-Dye2} \quad (I)$$

or the addition salts thereof with an acid, the electrical neutrality of the compounds is ensured by at least one cosmetically acceptable anion An, wherein Dye1, LK and Dye2 are as defined above, in contact with the wet or dry fibers, for a time that is sufficient to obtain the desired effect.

Another embodiment is a multi-compartment device comprising, at least one compartment, at least one composition comprising, in a medium that is suitable for dyeing keratin fibers, at least one compound of formula (I):

$$\text{Dye1-LK-Dye2} \quad (I)$$

or the addition salts thereof with an acid, the electrical neutrality of the compounds is ensured by at least one cosmetically acceptable anion An, wherein Dye1, LK and Dye2 are as defined above, and at least one compartment comprising an oxidizing composition.

In an embodiment compounds of formula (I):

$$\text{Dye1-LK-Dye2} \quad (I)$$

or the addition salts thereof with an acid, the electrical neutrality of the compounds is ensured by at least one cosmetically acceptable anion An, wherein Dye1, LK and Dye2 are as defined above, have at least one property chosen from good fastness with respect to external agents such as, for example, shampoos, even when the keratin fiber is sensitized; access to colorations that are less chromatic than those obtained with symmetrical compounds.

Other characteristics, aspects, subjects and advantages of the present disclosure will emerge even more clearly on reading the description and the concrete, but non-limiting, examples that follow.

For example, keratin fibers may be chosen from human keratin fibers, for example, the hair.

In an embodiment, Dye1 and Dye2 are such that the compound of formula (I) is not symmetrical; in other words, there is no axis or plane of symmetry passing through LK, said axis or plane of symmetry is coincident with or perpendicular to the main chain of LK.

As used herein:
an alkyl radical is linear and branched,
an alkyl radical or the alkyl part of a radical may be substituted with at least one substituent chosen from:
hydroxyl,
$C_1$-$C_4$ alkoxy, $C_2$-$C_4$ (poly)hydroxyalkoxy,
amino, amino substituted with at least one $C_1$-$C_4$ alkyl group, which may be identical or different, optionally bearing at least one hydroxyl group, said alkyl radicals optionally forming, with the nitrogen to which they are attached, a 5- or 6-membered heterocycle optionally comprising at least one other nitrogen or non-nitrogen hetero atom,
an aryl or heteroaryl radical or the aryl or heteroaryl part of a radical may be substituted at a carbon atom with at least one substituent chosen from:
a $C_1$-$C_{16}$, for example, $C_1$-$C_8$ alkyl radical, optionally substituted with at least one radical chosen from hydroxyl, $C_1$-$C_2$ alkoxy, $C_2$-$C_4$ (poly)hydroxyalkoxy, acylamino, amino substituted with two identical or different $C_1$-$C_4$ alkyl radicals, optionally bearing at least one hydroxyl group, or the two radicals optionally forming, with the nitrogen atom to which they are attached, a 5- to 7-membered, for example, 5- or 6-membered, heterocycle, optionally comprising another nitrogen or non-nitrogen hetero atom;

a halogen atom such as chlorine, fluorine or bromine;

a hydroxyl group;

a $C_1$-$C_2$ alkoxy radical; a $C_2$-$C_4$ (poly)hydroxyalkoxy radical;

an amino radical; an amino radical substituted with at least one $C_1$-$C_4$ alkyl radicals, which may be identical or different, optionally bearing at least one hydroxyl group, or amino with two optionally substituted $C_1$-$C_2$ alkyl radicals;

an acylamino radical (—NR—COR') wherein R is chosen from a hydrogen atom and a $C_1$-$C_4$ alkyl radical optionally bearing at least one hydroxyl group and R' is chosen from a $C_1$-$C_2$ alkyl radical; a carbamoyl radical ((R)$_2$N—CO—) wherein R, which may be identical or different, are each chosen from a hydrogen atom and a $C_1$-$C_4$ alkyl radical optionally bearing at least one hydroxyl group; an alkylsulfonylamino radical (R'SO$_2$—NR—) wherein R is chosen from a hydrogen atom and a $C_1$-$C_4$ alkyl radical optionally bearing at least one hydroxyl group and R' is chosen from a $C_1$-$C_4$ alkyl radical and a phenyl radical; an aminosulfonyl radical ((R)$_2$N—SO$_2$—) wherein R, which may be identical or different, are each chosen from a hydrogen atom and a $C_1$-$C_4$ alkyl radical optionally bearing at least one hydroxyl group, the cyclic or heterocyclic part of a non-aromatic radical may be substituted at a carbon atom with at least one substituent chosen from:

hydroxyl, $C_1$-$C_4$ alkoxy, $C_2$-$C_4$ (poly)hydroxyalkoxy, alkylcarbonylamino((RCO—NR'—) wherein R' is chosen from a hydrogen atom and a $C_1$-$C_4$ alkyl radical optionally bearing at least one hydroxyl group and R is chosen from a $C_1$-$C_2$ alkyl radical, and an amino radical substituted with two identical or different $C_1$-$C_4$ alkyl groups optionally bearing at least one hydroxyl group, said alkyl radicals optionally forming, with the nitrogen atom to which they are attached, a 5- or 6-membered heterocycle optionally comprising at least one other nitrogen or non-nitrogen hetero atom.

In an embodiment, $R_1$, $R'_1$, $R'_2$ and $R'_3$, which may be identical or different, are chosen from:

a hydrogen atom;

an optionally substituted $C_1$-$C_6$ alkyl radical;

an aryl and arylalkyl radical, such as phenyl or benzyl, the aryl part is optionally substituted;

$R_1$ may form, with all or part of the group LK and with the nitrogen atom to which each is attached, a saturated and unsaturated, aromatic and non-aromatic, optionally substituted 5- to 7-membered heterocycle;

$R'_1$, $R'_2$ or $R'_3$ together or separately, may form, with all or part of the group LK and with the nitrogen or oxygen atom to which each is attached, a saturated and unsaturated, aromatic and non-aromatic, optionally substituted 5- to 7-membered heterocycle.

In another embodiment, $R_1$, $R'_1$, $R'_2$ and $R'_3$, which may be identical or different, are chosen from:

a hydrogen atom;

an optionally substituted $C_1$-$C_3$ alkyl radical, such as methyl, ethyl, 2-hydroxyethyl or 2-methoxyethyl;

a phenyl radical; optionally substituted with at least one radical chosen from hydroxyl, $C_1$-$C_2$ alkoxy and amino radicals and amino radicals substituted with at least one $C_1$-$C_4$ groups optionally bearing at least one hydroxyl group;

$R_1$ or $R'_2$ and $R'_3$ may form, with the nitrogen, or oxygen atom for $R'_3$, to which each is attached and all or part of the group LK, a 5- to 7-membered heterocycle chosen from pyrrolidines, piperidines, piperazines and homopiperazines optionally substituted with at least one radical chosen from methyl, hydroxyl, amino and (di)methylamino radicals.

In another embodiment, $R_1$, $R'_1$, $R'_2$ and $R'_3$, which may be identical or different, are chosen from:

a hydrogen atom;

methyl, ethyl and 2-hydroxyethyl radicals;

a phenyl radical, optionally substituted with a radical chosen from hydroxyl, methoxy, amino, (di)methylamino and (di)(2-hydroxyethyl)amino radicals;

$R_1$ or $R'_2$ and $R'_3$ may form, with the nitrogen, or oxygen atom for $R'_3$, to which each is attached and all or part of the group LK, a 5- to 7-membered heterocycle chosen from pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl)piperidine, 4-(dimethylamino)piperidine, piperazine, 1-methylpiperazine, 1-(2-hydroxyethyl) piperazine, 1-(2-aminoethyl)piperazine, 1-hydroxyethylethoxypiperazine, homopiperazine and 1-methyl-1,4-perhydrodiazepine.

In one embodiment, $R_4$, $R_5$, $R_6$, $R'_6$, $R_7$, $R_8$, $R_{10}$ and $R_{11}$, which may be identical or different, for example, are chosen from:

a hydrogen atom for $R_4$, $R_5$, $R_7$, $R_8$, $R_{10}$ and $R_{11}$;

an, optionally substituted $C_1$-$C_{16}$, for example, $C_1$-$C_8$, alkyl radical;

a halogen atom such as chlorine, fluorine or bromine;

a hydroxyl group;

a $C_1$-$C_2$ alkoxy radical; a $C_2$-$C_4$ (poly)hydroxyalkoxy radical;

an amino radical; an amino radical substituted with one or two $C_1$-$C_4$ alkyl radicals, which may be identical or different, optionally bearing at least one group chosen from a hydroxyl and $C_1$-$C_4$ dialkylamino groups;

an alkylcarbonylamino radical (RCO—NR'—) wherein R is chosen from a $C_1$-$C_4$ alkyl radical and R' is chosen from a hydrogen and a $C_1$-$C_4$ alkyl radical; a carbamoyl radical ((R)$_2$N—CO—) wherein R, which may be identical or different, are each chosen from a hydrogen atom and a $C_1$-$C_4$ alkyl radical optionally bearing at least one hydroxyl group; an alkylsulfonylamino radical (R'SO$_2$—NR—) wherein R is chosen from a hydrogen atom and a $C_1$-$C_4$ alkyl radical optionally bearing at least one hydroxyl group, R' is chosen from a $C_1$-$C_4$ alkyl radical; an aminosulfonyl radical ((R)$_2$N—SO$_2$—) wherein R, which may be identical or different, are each chosen from a hydrogen atom and a $C_1$-$C_4$ alkyl radical optionally bearing at least one hydroxyl group; and a bond from $W'_2$ to $W'_1$ or to the group LK, or from $W'_5$ to $W'_6$ or to the group LK.

In another embodiment, $R_4$, $R_5$, $R_6$, $R'_6$, $R_7$, $R_8$, $R_{10}$ and $R_{11}$, which identical or different, for example, are chosen from:

a hydrogen atom for $R_4$, $R_5$, $R_6$, $R'_6$, $R_7$, $R_8$, $R_{10}$ and $R_{11}$;

a $C_1$-$C_4$ alkyl radical optionally substituted with at least one radical chosen from hydroxyl and acylamino radicals, or amino radicals substituted with two identical or different $C_1$-$C_2$ alkyl radicals, optionally bearing at least one hydroxyl group, or a $C_1$-$C_2$ alkoxy radical;

an amino radical; an amino radical substituted with one or two identical or different $C_1$-$C_2$ alkyl radicals, optionally bearing at least one hydroxyl group; an acylamino radical; a carbamoyl radical; a sulfonylamino radical;

a hydroxyl radical; a $C_1$-$C_2$ alkoxy radical; and a bond from $W'_2$ to $W'_1$ or to the group LK, or from $W'_5$ to $W'_6$ or to the group LK.

In another embodiment, $R_4$, $R_5$, $R_6$, $R'_6$, $R_7$, $R_8$, $R_{10}$ and $R_{11}$, which may be identical or different, for example, are chosen from:

a hydrogen atom for $R_4$, $R_5$, $R_6$, $R'_6$, $R_7$, $R_8$, $R_{10}$ and $R_{11}$;

a methyl, ethyl, propyl, 2-hydroxyethyl, methoxy, ethoxy, 2-hydroxyethyloxy, 3-hydroxypropyloxy or 2-methoxyethyl radical;

a sulfonylamino radical; an amino, methylamino, dimethylamino, 2-hydroxyethylamino, 3-hydroxypropylamino or acylamino radical; a hydroxyl radical;

chlorine atoms; and bonds from $W'_2$ to $W'_1$ or to the group LK, or from $W'_5$ to $W'_6$ or to the group LK.

$R_9$ may be, for example, chosen from a hydrogen atom or a $C_1$-$C_{15}$ alkyl radical; a $C_2$-$C_6$ monohydroxyalkyl radical; a $C_2$-$C_6$-polyhydroxyalkyl radical; a ($C_1$-$C_6$)alkoxy($C_2$-$C_6$) alkyl radical; an optionally substituted aryl radical, such as phenyl; an optionally substituted arylalkyl radical, such as benzyl; a $C_2$-$C_6$ amidoalkyl radical; and a $C_2$-$C_6$ aminoalkyl radical, the amine of which is substituted with two identical or different, optionally substituted $C_1$-$C_4$ alkyl radicals; wherein $R_9$ is such that the atom directly linked to the nitrogen atom is a carbon atom.

For example, $R_9$ may be chosen from a hydrogen atom, a $C_1$-$C_6$ alkyl radical or a $C_2$-$C_6$ monohydroxyalkyl radical; a $C_2$-$C_6$ polyhydroxyalkyl radical; a ($C_1$-$C_6$)alkoxy($C_2$-$C_6$) alkyl radical; a phenyl radical optionally substituted with at least one chlorine atom, a hydroxyl group, a group RCO—NH— wherein R is chosen from a $C_1$-$C_4$ alkyl radical or an amino radical substituted with two identical or different $C_1$-$C_4$ alkyl radicals; a benzyl radical; a $C_1$-$C_6$ aminoalkyl radical; and a $C_1$-$C_6$ aminoalkyl radical wherein the amine is substituted with two identical or different $C_1$-$C_4$ alkyl radicals; wherein $R_9$ is such that the atom directly linked to the nitrogen atom is a carbon atom.

According to one embodiment, $W_2$, $W_5$, $W'_2$ and $W'_5$, which may be identical or different, are each chosen from group of formula (a) or (c).

According to this embodiment $X_1$ for example, is chosen from a group $CR_7$.

For example, according to this embodiment, $X_2$ is chosen from a radical $CR_8$.

For example, according to this embodiment, $R_4$, $R_5$, $R_6$, $R'_6$, $R_7$ and $R_8$, which may be identical or different, have the same meanings as above.

W₃ and W₄, which may be identical or different, for example, are each chosen from heterocycle of formulae (1) to (3) below:

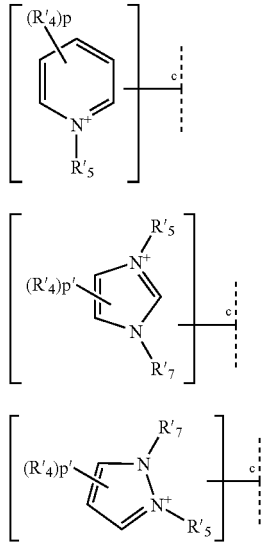

wherein $R'_4$, $R'_5$, $R'_7$, p, p' and c are defined as above.

In one embodiment of the disclosure, $W_3$ and $W_4$ are not simultaneously chosen from imidazolium group.

For example, $R'_5$ and $R'_7$ have the same definitions as $R_9$, with the exception of hydrogen.

In one embodiment of the disclosure, the cationic aromatic heterocyclic group is chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium.

According to another embodiment of the disclosure, $W_3$ and $W_4$, which may be identical or different, are each chosen from cationic aromatic heterocycles chosen from 2-imidazolium, 2-pyridinium, 3-pyridinium, 4-pyridinium, 2-quinolinium, 4-quinolinium, 3-pyrazolium, 4-pyrazolium, 3-indazolium, 4-indazolium and 7-indazolium.

In one embodiment of the disclosure, LK may be chose from:

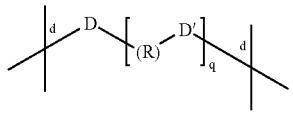

wherein
D and D', which may be identical or different, are each chosen from linear and branched, saturated and unsaturated $C_1$-$C_{14}$ hydrocarbon-based bonds, optionally interrupted with at least one hetero atoms or with at least one groups bearing at least one hetero atom, for example, chosen from oxygen and nitrogen;
the bond d links the arms D and D' to the groups $W_1$, $W_6$, $W'_2$ and $W'_5$;
q is greater than or equal to 1, for example, equal to 1 or 2;

the group R is chosen from

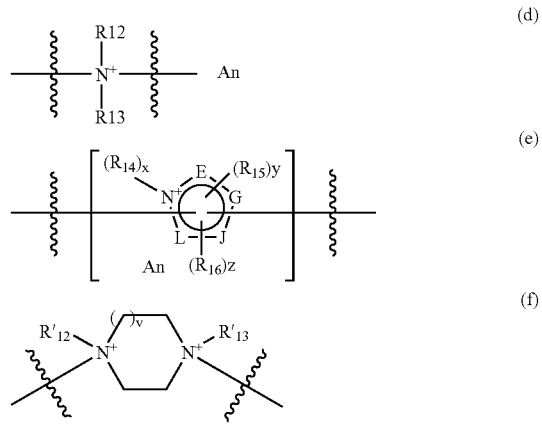

$R_{12}$, $R_{13}$, $R'_{12}$ and $R'_{13}$, which may be identical or different, are each chosen from a $C_1$-$C_{15}$ alkyl radical; a $C_1$-$C_6$ monohydroxyalkyl radical; a $C_2$-$C_6$ polyhydroxy-alkyl radical; a $(C_1$-$C_6)$alkoxy$(C_1$-$C_6)$alkyl radical; an aryl radical such as phenyl; an arylalkyl radical such as benzyl; a $C_1$-$C_6$ amidoalkyl radical; a $C_1$-$C_6$ aminoalkyl radical; a $C_1$-$C_6$ aminoalkyl radical wherein the amine is substituted with at least one identical or different $C_1$-$C_4$ alkyl, $(C_1$-$C_6)$alkylcarbonyl, acylamino or $(C_1$-$C_6)$alkylsulfonyl radicals;

$R_{12}$ and $R_{13}$ may form, together with the nitrogen atom to which they are attached, a 5-, 6- or 7-membered saturated cationic ring that may comprise at least one hetero atoms, the cationic ring optionally is substituted with a halogen atom, a hydroxyl radical, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a $(C_1$-$C_6)$alkylcarbonyl radical, a thio radical, a $C_1$-$C_6$ thioalkyl radical, a $(C_1$-$C_6)$alkylthio radical, an amino radical and an amino radical substituted with at least one identical or different $C_1$-$C_6$ alkyl, $(C_1$-$C_6)$alkylcarbonyl, acylamino or $(C_1$-$C_6)$alkylsulfonyl radicals; for example, the cationic ring is unsubstituted;

$R_{12}$ or $R_{13}$ may form, with D or D', a 5-, 6- or 7-membered saturated cationic ring that may comprise at least one hetero atoms, the cationic ring optionally is substituted with a halogen atom, a hydroxyl radical, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a $(C_1$-$C_6)$alkylcarbonyl radical, a thio radical, a $C_1$-$C_6$ thioalkyl radical, a $(C_1$-$C_6)$alkylthio radical, an amino radical and an amino radical substituted with at least one identical or different $C_1$-$C_6$ alkyl, $(C_1$-$C_6)$alkyl-carbonyl, acylamino or $(C_1$-$C_6)$alkylsulfonyl radicals; for example, the cationic ring is unsubstituted;

$R_{12}$ and $R_{13}$ may form with $W_1$ or $W_6$ a 5-, 6- or 7-membered, saturated and unsaturated, aromatic and non-aromatic, optionally substituted cationic heterocycle; the ring;

the ring members E, G, J and L, which may be identical or different, are each chosen from carbon, oxygen, sulfur or nitrogen atom to form a ring chosen from pyrazolium, imidazolium, triazolium, oxazolium, isoxazolium, thiazolium and isothiazolium rings, $R_{14}$ has the same meaning as $R_{12}$;

$R_{15}$ is chosen from a $C_1$-$C_6$ alkyl radical; a $C_1$-$C_6$ monohydroxyalkyl radical, a $C_2$-$C_6$ polyhydroxyalkyl radical, a $(C_1$-$C_6)$alkoxy$(C_1$-$C_6)$alkyl radical, a $C_2$-$C_6$ carbamylalkyl radical, a $(C_1$-$C_6)$alkylcarboxy$(C_1$-$C_6)$alkyl radical and a benzyl radical; wherein $R_{15}$ is attached to a nitrogen atom, $R_{16}$, which may be identical or different, are each chosen from hydrogen or halogen atom, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a carboxyl radical, a $C_1$-$C_6$ alkylcarbonyl radical, a $C_1$-$C_6$ thioalkyl radical, a $(C_1$-$C_6)$alkylthio radical, an amino radical disubstituted with a $(C_1$-$C_6)$alkyl, $(C_1$-$C_6)$alkylcarbonyl or $(C_1$-$C_6)$alkylsulfonyl radical, a benzyl radical, and a phenyl radical optionally substituted with at least one radical chosen from methyl, hydroxyl, amino and methoxy radicals, wherein, $R_{16}$ is attached to a carbon atom, An is chosen from an organic or mineral anion;

z is an number ranging from 1 to 3;

y is equal to 0 or 1;

v is equal to 1 or 2;

x is equal to 0 or 1;

wherein x=0, then one of the linker arms D or D' is attached to the quaternized nitrogen atom, wherein x=1, at least one of the linker arms D and/or D' is attached to a carbon atom.

According to one embodiment of formula (d), $R_{12}$ and $R_{13}$, which may be identical or different, are for example, chosen from a $C_1$-$C_6$ alkyl radical, a $C_1$-$C_4$ monohydroxyalkyl radical, a $C_2$-$C_4$ polyhydroxyalkyl radical, a $(C_1$-$C_6)$alkoxy$(C_2$-$C_4)$alkyl radical, a $C_2$-$C_6$ amidoalkyl radical or a $C_2$-$C_6$ dimethylaminoalkyl radical.

By further example, $R_{12}$ and $R_{13}$, which may be identical or different, are each chosen from methyl, ethyl or 2-hydroxyethyl radical.

According to this embodiment, D and D', which may be identical or different, are for example, a $C_1$-$C_6$ alkyl chain that may be substituted, and is, for example, unsubstituted.

According to one embodiment of formula (e), the ring members E, G, J and L form a ring chosen from imidazolium, pyrazolium, oxazolium and thiazolium rings.

According to this embodiment, x and b are equal to 0.

In this embodiment, D and D' are each chosen from $C_1$-$C_4$ alkyl chain that may be substituted, and is, for example, unsubstituted.

Moreover, $R_{14}$, for example, is chosen from a methyl, ethyl and 2-hydroxyethyl radical.

According to one embodiment of formula (f), $R'_{12}$ and $R'_{13}$ have the same meanings as $R_{12}$ and $R_{13}$.

According to this embodiment, D and D', which may be identical or different, are, for example, a $C_1$-$C_6$ alkyl chain that may be substituted, and is, for example, unsubstituted.

For example, in one embodiment, the coefficient v is equal to 1.

An may be chosen from an organic or mineral anion or mixture of anions, so as to respect the electrical neutrality of the compound, for example chosen from halides such as chlorides, bromides, fluorides or iodides; hydroxides; sulfates; hydrogen sulfates; $(C_1$-$C_6)$alkyl sulfates, for instance methyl sulfate or ethyl sulfate; phosphates; carbonates; hydrogen carbonates; perchlorates; acetates; tartrates; citrates; oxalates; $(C_1$-$C_6)$-alkylsulfonates such as methylsulfonate; and arylsulfonates, which are unsubstituted or substituted with a $C_1$-$C_4$ alkyl radical, for instance a 4-tolylsulfonate.

The addition salts with an acid of the compounds of formula (I) may be chosen from, for example, halides, for instance chlorides or bromides, sulfates, alkyl sulfates for which the linear and branched alkyl part is of $C_1$-$C_6$, for instance methosulfate or ethosulfate ions, hydrogen carbonates, perchlorates, carboxylic acid salts, for instance acetates; citrates; tartrates, alone or in combination.

In one embodiment of the disclosure, the compounds of formula (I) are chosen from:

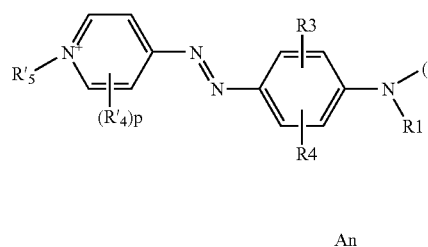
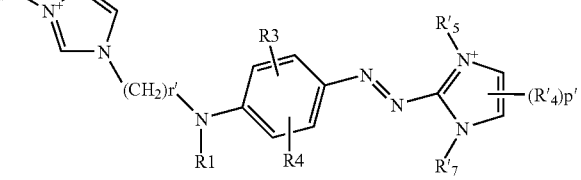

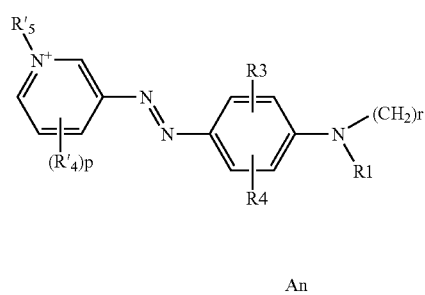
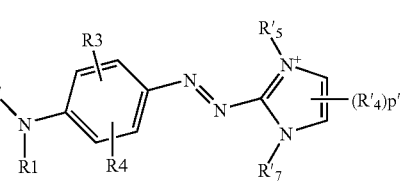

-continued
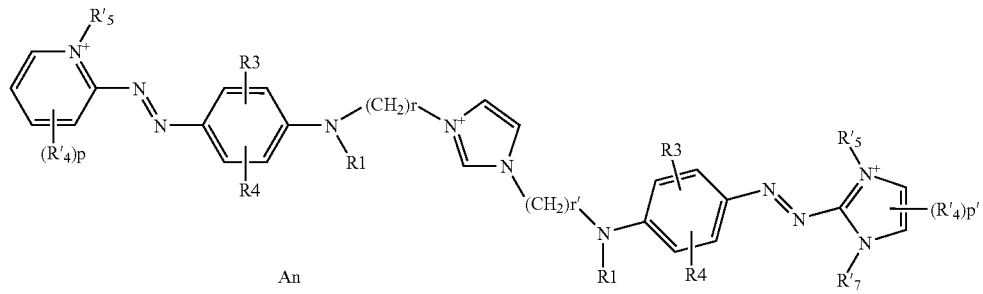
An
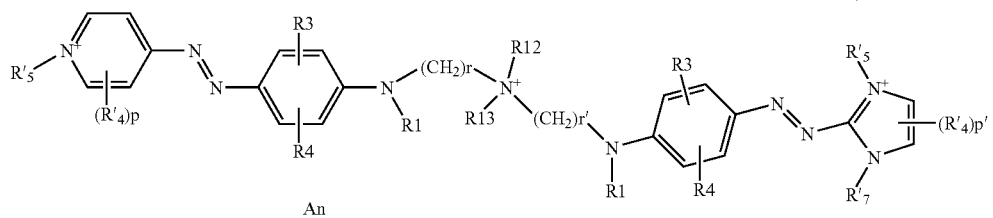
An
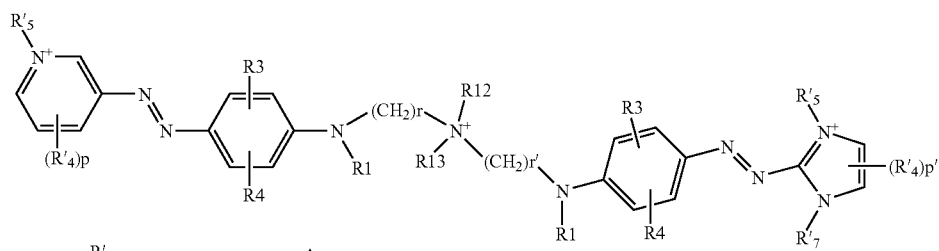
An
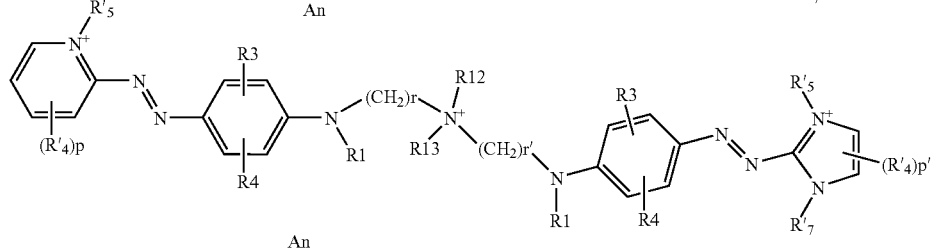
An
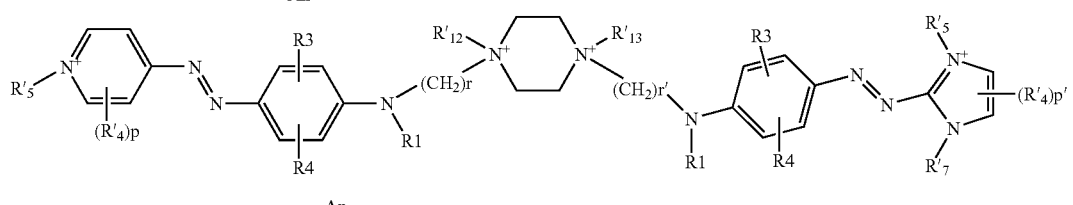
An
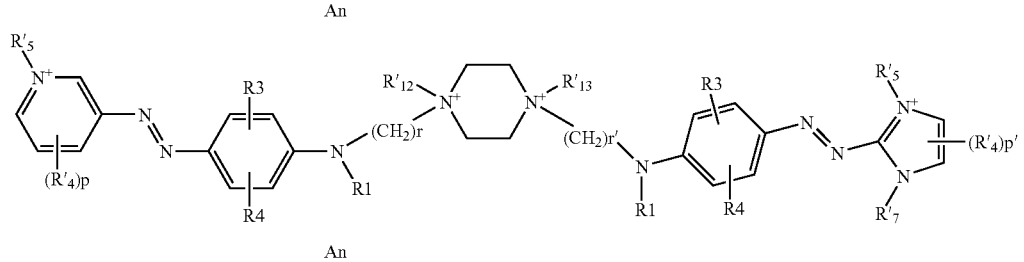
An
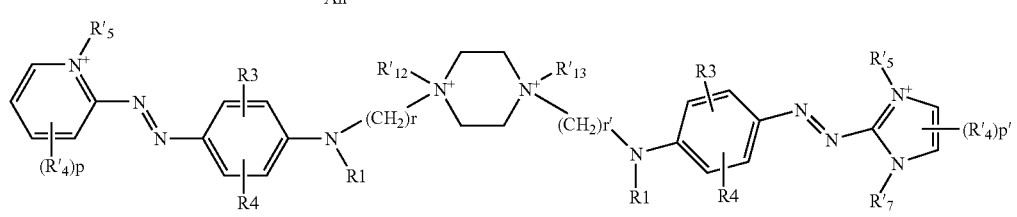
An -continued

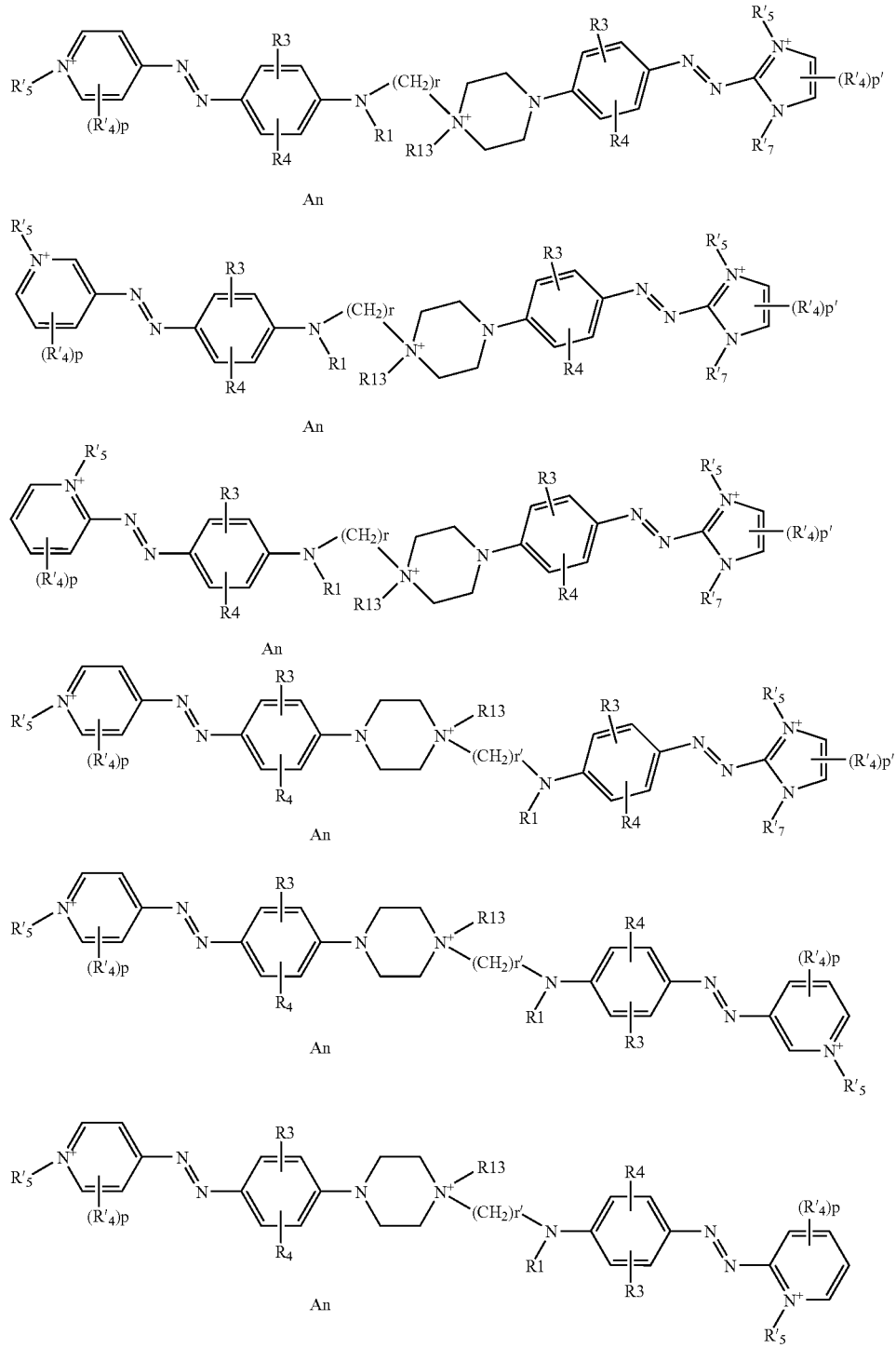

wherein formulae:
R$_1$, R$_3$, R$_4$, R$_{12}$, R$_{13}$, R'$_4$, R'$_5$, R'$_7$, R'$_{12}$, R'$_{13}$, p and p' are defined as above;
r and r', which may be identical or different, are numbers ranging from 1 to 10, for example, from 1 to 6;
wherein, the electrical neutrality of the molecule is respected by the presence of at least one cosmetically acceptable anion An as defined above.

For example, R$_3$, R$_4$ and R'$_4$ are each chosen from a hydrogen atom.

These compounds may be obtained from preparation processes described, for example, in documents U.S. Pat. No. 5,708,151, J. Chem. Res., Synop. (1998), (10), 648-649, U.S. Pat. Nos. 3,151,106, 5,852,179, Heterocycles, 1987, 26 (2) 313-317, Synth. Commun. 1999, 29(13), 2271-2276, Tetrahedron, 1983, 39(7), 1091-1101.

Another embodiment is a composition comprising, in a medium that is suitable for dyeing keratin fibers, at least one compound of formula (I), or an addition salt thereof with an acid, as direct dye, wherein DYE1, LK and DYE2 are defined as above.

The concentration of the at least one compound of formula (I) may range from 0.001% to 20% by weight, for example, from 0.01% to 10% by weight and further, for example, from 0.05% to 5% by weight, relative to the total weight of the dye composition.

In one embodiment, the composition according to the disclosure may also comprise at least one oxidation base. This at least one oxidation base may be chosen from the oxidation bases conventionally used in oxidation dyeing, for example ortho-phenylenediamines, para-phenylenediamines, double bases such as bis(phenyl)alkylenediamines; para-aminophenols, ortho-aminophenols and heterocyclic bases and the addition salts thereof with an acid.

Among the para-phenylenediamines that may be mentioned are, for example, para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, and the addition salts thereof with an acid.

For example, the para-phenylenediamines may be chosen from para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis-(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino-3-hydroxymethylphenyol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof with an acid.

Among the heterocyclic bases that may be mentioned, for example, are pyridine derivatives, pyrimidine derivatives and pyrazole derivatives.

Among the pyridine derivatives that may be mentioned are the compounds described, for example, in UK Patent Nos. GB 1 026 978 and GB 1 153 196, such as 2,5-diaminopyridine, 2-(4-methoxyphenyl)amino-3-aminopyridine, 2,3-diamino-6-methoxy-pyridine, 2-(β-methoxyethyl)amino-3-amino-6-methoxypyridine and 3,4-diaminopyridine, and the addition salts thereof with an acid.

Among the pyrimidine derivatives that may be mentioned are the compounds described, for example, in German Patent No. DE 2 359 399; Japanese Patent Nos. JP 88-169 571; JP 05-163 124; and European Patent No. EP 0 770 375 or PCT Patent Application No. WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in French Patent Application No. FR-A-2 750 048 and among which non-limiting mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxy-ethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]-pyrimidine, and the addition salts thereof with an acid and the tautomeric forms thereof, when a tautomeric equilibrium exists.

Among the pyrazole derivatives that may be mentioned are the compounds described in German Patent Nos. DE 3 843 892 and DE 4 133 957 and PCT Patent Application Nos. WO 94/08969, WO 94/08970, French Patent Application No. FR-A-2 733 749 and German Patent Application No. DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4- methylaminopyrazole and 3,5-diamino-4-(β-hydroxyethyl) amino-1-methylpyrazole, and the addition salts thereof with an acid.

The composition according to the disclosure may also comprise at least one couplers conventionally used for dyeing keratin fibers. Among these couplers, non-limiting mention may be made, for example, of meta-phenylenediamines, meta-aminophenols, meta-diphenols, naphthalene-based couplers and heterocyclic couplers, the addition salts thereof with an acid, and also mixtures thereof.

Couplers that may be mentioned are chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxy-ethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)-amino-3,4-methylenedioxybenzene and 2,6-bis(β-hydroxyethylamino) toluene and the addition salts thereof with an acid.

In the composition of the present disclosure, the at least one coupler may be present in an amount ranging from 0.001% to 10% by weight, for example, from 0.005% to 6% by weight, relative to the total weight of the dye composition. The at least one oxidation base may be present in an amount, for example, ranging from 0.001% to 10% by weight, and further, for example, from 0.005% to 6% by weight, relative to the total weight of the dye composition.

For example, the addition salts with an acid that may be used in the context of the dye compositions of the disclosure for the oxidation bases and couplers are chosen, for example, from the hydrochlorides, hydrobromides, sulfates, citrates, succinates, tartrates, lactates, tosylates, benzenesulfonates, phosphates and acetates.

The composition according to the disclosure may optionally comprise at least one additional direct dye other than the compounds of formula (I). This dye may be chosen from cationic and nonionic species.

Non-limiting-examples of the at least one additional direct dye that may-be mentioned are chosen from nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes, alone or as mixtures.

The at least one additional direct dye may be chosen, for example, from the following red or orange nitrobenzene dyes:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The at least one additional direct dye may also be chosen from yellow and green-yellow nitrobenzene direct dyes; non-limiting mention may be made, for example, -of the compounds chosen from:
1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulfonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Mention may also be made of blue or violet nitrobenzene direct dyes, for instance:
1-(β-hydroxyethyl)amino-4-N,N-bis(β-hydroxyethyl) amino-2-nitrobenzene,
1-(γ-hydroxypropyl)amino-4,N,N-bis(β-hydroxyethyl) amino-2-nitrobenzene,
1-(β-hydroxyethyl)amino-4-(N-methyl-N-β-hydroxyethyl) amino-2-nitrobenzene,
1-(β-hydroxyethyl)amino-4-(N-ethyl-N-β-hydroxyethyl) amino-2-nitrobenzene,
1-(β,γ-dihydroxypropyl)amino-4-(N-ethyl-N-β-hydroxyethyl)amino-2-nitrobenzene,
2-nitro-para-phenylenediamines of the following formula:

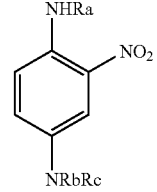

wherein:
R$_b$ is chosen from a C$_1$-C$_4$ alkyl radical and a β-hydroxyethyl, β-hydroxypropyl and γ-hydroxypropyl radical;
R$_a$ and R$_c$, which may be identical or different, are each chosen from β-hydroxyethyl, β-hydroxypropyl, γ-hydroxypropyl and β,γ-dihydroxypropyl radicals, wherein at least one of R$_b$, R$_c$ or R$_a$ is chosen from a γ-hydroxypropyl radical wherein $R_b$ and $R_c$ are not simultaneously a β-hydroxyethyl radical when $R_b$ is a γ-hydroxypropyl radical, such as those described in French Patent No. FR 2 692 572.

Among the azo direct dyes that may be used according to the disclosure, non-limiting mention may be made of the cationic azo dyes described in PCT Patent Application Nos. WO 95/15144, WO 95/01772 and European Patent Application No. EP 714 954.

Among azo direct dyes, non-limiting mention may be made of the following dyes:

1,3-dimethyl-2-[[4-(dimethylamino)phenyl]azo]-1H-imidazolium chloride, 1,3-dimethyl-2-[(4-aminophenyl)azo]-1H-imidazolium chloride, 1-methyl-4-[(methylphenylhydrazono)methyl]pyridinium methyl sulfate.

Among the azo direct dyes that may also be mentioned are the following dyes described in the Color Index International 3rd edition:

Disperse Red 17
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24
Disperse Black 9.

Mention may also be made of 1-(4'-aminodiphenylazo)-2-methyl-4-[bis(β-hydroxyethyl)amino]benzene and 4-hydroxy-3-(2-methoxyphenylazo)-1-naphthalenesulfonic acid.

Among the quinone direct dyes that may be mentioned are the following dyes:

Disperse Red 15
Solvent Violet 13
Acid Violet 43
Disperse Violet 1
Disperse Violet 4
Disperse Blue 1
Disperse Violet 8
Disperse Blue 3
Disperse Red 11
Acid Blue 62
Disperse Blue 7
Basic Blue 22
Disperse Violet 15
Basic Blue 99 and also the following compounds:

1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes that may be mentioned are the following compounds:

Basic Blue 17
Basic Red 2.

Among the triarylmethane dyes that may be used according to the disclosure, non-limiting mention may be made of the following compounds:

Basic Green 1
Acid Blue 9
Basic Violet 3
Basic Violet 14
Basic Blue 7
Acid Violet 49
Basic Blue 26
Acid Blue 7.

Among the indoamine dyes that may be used according to the disclosure, non-limiting mention may be made of the following compounds:

2-β-hydroxyethylamino-5-[bis(β-4'-hydroxyethyl)amino]anilino-1,4-benzoquinone;

2-β-hydroxyethylamino-5-(2'-methoxy-4'-amino)anilino-1,4-benzoquinone;

3-N(2'-chloro-4'-hydroxy)phenylacetylamino-6-methoxy-1,4-benzoquinoneimine;

3-N(3'-chloro-4'-methylamino)phenylureido-6-methyl-1,4-benzoquinoneimine;

3-[4'-N-(ethylcarbamylmethyl)amino]phenylureido-6-methyl-1,4-benzoquinoneimine.

Among the dyes of tetraazapentamethine type that may be used according to the disclosure, non-limiting mention may be made of the following compounds, wherein An is defined as above:

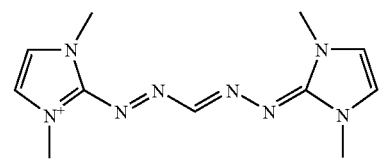

An

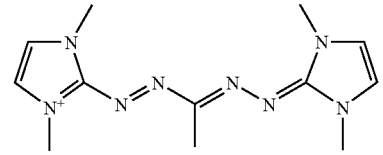

An

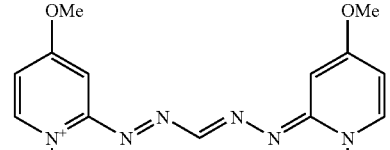

An

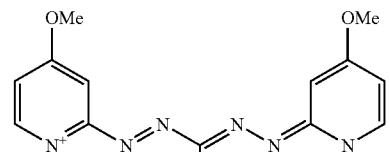

An

-continued

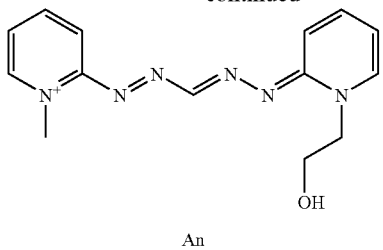

An

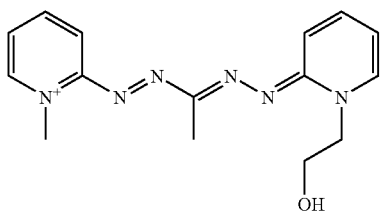

An

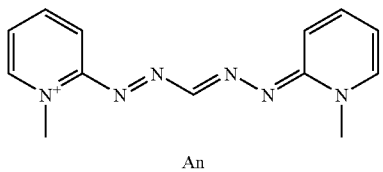

An

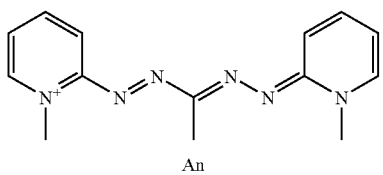

An

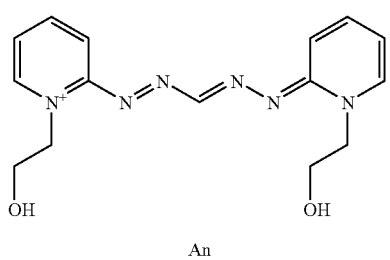

An

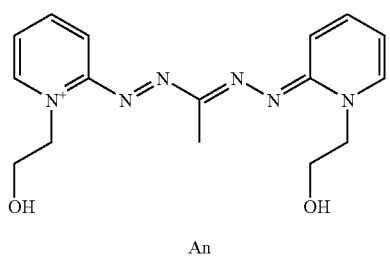

An

Among the natural direct dyes that may be used according to the disclosure, non-limiting mention may be made of lawsone, juglone, alizarin, purpurin, carminic acid, kermesic acid, purpurogallin, protocatechaldehyde, indigo, isatin, curcumin, spinulosin and apigenidin. Extracts or decoctions comprising these natural dyes may also be used, for example, henna-based poultices or extracts.

The at least one additional direct dye may be present in an amount ranging from 0.001% to 20% by weight, relative to the weight of the composition, for example, from 0.01% to 10% by weight, relative to the weight of the composition.

The medium that is suitable for dyeing, also known as the dye support, may comprise water or of a mixture of water and of at least one organic solvent to dissolve the compounds that are not sufficiently water-soluble.

For example, the at least one organic solvent may be chosen from linear and branched, for example, saturated, monoalcohols or diols comprising from 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ether, propylene glycol and its ethers, for instance propylene glycol monomethyl ether, butylene glycol and dipropylene glycol; and also diethylene glycol alkyl ethers, for example, of $C_1$-$C_4$, for instance diethylene glycol monoethyl ether or monobutyl ether, alone or as a mixture.

The at least one organic solvent may be present in an amount ranging from 1% to 40% by weight, for example, from 5% to 30% by weight, relative to the total weight of the composition.

The dye composition disclosed herein may also comprise at least one adjuvant conventionally used in compositions for dyeing the hair chosen from anionic, cationic, nonionic, amphoteric or zwitterionic surfactants or mixtures thereof, anionic, cationic, nonionic, amphoteric or zwitterionic polymers or mixtures thereof, mineral or organic thickeners, for example, anionic, cationic, nonionic and amphoteric associative polymeric thickeners, antioxidants, penetrating agents, sequestering agents, fragrances, buffers, dispersants, conditioning agents, for instance silicones, which may or may not be volatile or modified, film-forming agents, ceramides, preserving agents and opacifiers.

The at least one adjuvants may be present in an amount ranging from 0.01% and 20% by weight, relative to the weight of the composition.

A person skilled in the art will take care to select these optional additional compounds such that the advantageous properties intrinsically associated with the oxidation dye composition of the disclosure are not, or are not substantially, adversely affected by the envisaged addition(s).

The pH of the dye composition of the disclosure ranges from 3 to 12, for example, from 5 to 11. It may be adjusted to the desired value using one or more acidifying or basifying agents usually used in the dyeing of keratin fibers, or by using standard buffer systems.

Among the acidifying agents that may be mentioned, for example, are mineral or organic acids such as hydrochloric acid, orthophosphoric acid, sulfuric acid, carboxylic acids such as acetic acid, tartaric acid, citric acid and lactic acid, and sulfonic acids.

Among the basifying agents that may be mentioned, for example, are aqueous ammonia, alkaline carbonates, alkanolamines such as monoethanolamine, diethanolamine and triethanolamine and derivatives thereof, sodium hydroxide, potassium hydroxide and the compounds of the following formula:

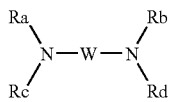

wherein W is a propylene residue optionally substituted with a hydroxyl group or a $C_1$-$C_4$ alkyl radical; $R_a$, $R_b$, $R_c$ and $R_d$, which may be identical or different, are each chosen from a hydrogen atom, a $C_1$-$C_4$ alkyl radical or a $C_1$-$C_4$ hydroxyalkyl radical.

The dye composition according to the disclosure may be in various forms chosen from liquids, creams or gels, and in any other form that is suitable for dyeing keratin fibers, for example, human hair.

The composition according to the disclosure may also comprise at least one oxidizing agent. In this case, the composition is referred to as a ready-to-use composition.

For the purposes of the present disclosure, the term "ready-to-use composition" means a composition intended to be applied immediately to the keratin fibers, i.e. it may be stored in unmodified form before use or may result from the extemporaneous mixing of two or more compositions.

The composition according to the disclosure may also be obtained by mixing the composition according to the disclosure with an oxidizing composition.

The at least one oxidizing agent may be any oxidizing agent conventionally used in the field. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases, for instance laccases. For example, the oxidizing agent may be hydrogen peroxide.

The content of oxidizing agent ranges from 1% to 40% by weight relative to the weight of the ready-to-use composition, for example, from 1% to 20% by weight relative to the weight of the ready-to-use composition.

For example, the oxidizing composition used may be an aqueous composition and may be in the form of a solution or an emulsion.

For example, the composition free of oxidizing agent may be mixed with 0.5 to 10 weight equivalents of the oxidizing composition.

The pH of the ready-to-use composition may, for example, range from 4 to 12, for example, from 7 to 11.5.

The pH of the composition may be adjusted using an acidifying or basifying agent chose, for example, from those mentioned previously in the context of the description according to the disclosure.

Another embodiment of the disclosure is also a dyeing process that comprises the application of a dye composition according to the disclosure to wet or dry keratin fibers.

The application to the fibers of the dye composition comprising the compound(s) of formula (I) or the addition salts thereof with an acid, optionally at least one oxidation base optionally combined with at least one coupler, and optionally at least one additional direct dye, may be performed in the presence of an oxidizing agent.

This oxidizing agent may be added to the composition comprising the at least one compound of formula (I) and the optional oxidation bases, couplers and optional additional direct dyes, either at the time of use or directly onto the keratin fiber.

The oxidizing composition may also comprise various adjuvants conventionally used in compositions for dyeing the hair and as defined above.

The pH of the oxidizing composition comprising the oxidizing agent is such that, after mixing with the dye composition, the pH of the resulting composition applied to the keratin fibers may, for example, range from 4 to 12, for example, from 7 to 11.5. It may be adjusted to the desired value by means of acidifying or basifying agents usually used in the dyeing of keratin fibers and as defined above.

The composition that is finally applied to the keratin fibers may be in various forms chosen from liquids, creams, gels and in any other form that is suitable for dyeing keratin fibers, for example, human hair.

According to one embodiment, the composition according to the disclosure is free of oxidation base and of coupler.

The composition applied may optionally comprise at least one oxidizing agent.

The composition is thus applied to the wet or dry keratin fibers and is then: left for a leave-in time that is sufficient to obtain the desired coloration.

Whatever the embodiment adopted (with or without oxidizing agent), the leave-in time ranges from a few seconds to one hour, for example, ranging from 3 to 30 minutes.

The temperature at which the composition is left to act may range from 15 to 220° C., for example, from 15 to 80° C. and further, for example, from 15 to 40° C.

After the leave-in time, the composition is removed by rinsing with water, optionally followed by washing with a shampoo, and then optionally drying.

Another embodiment of the disclosure is a multi-compartment device or dyeing "kit" wherein at least one compartment comprises at least one dye composition of the disclosure and at least one compartment comprises at least one oxidizing composition. This device may be equipped with a means for applying the desired mixture to the hair, such as the devices described in French Patent No. FR-2 586 913.

Other than in the operating examples, and where otherwise indicated, all numbers expressing quantities of ingredients, reaction conditions, and so forth used in the specification and claims are to be understood as modified in all instances by the term "about." Accordingly, unless indicated to the contrary, the numerical parameters set forth in this specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The following examples are intended to illustrate the disclosure in a non-limiting manner.

EXAMPLE 1
1/Synthesis of Compound 6:
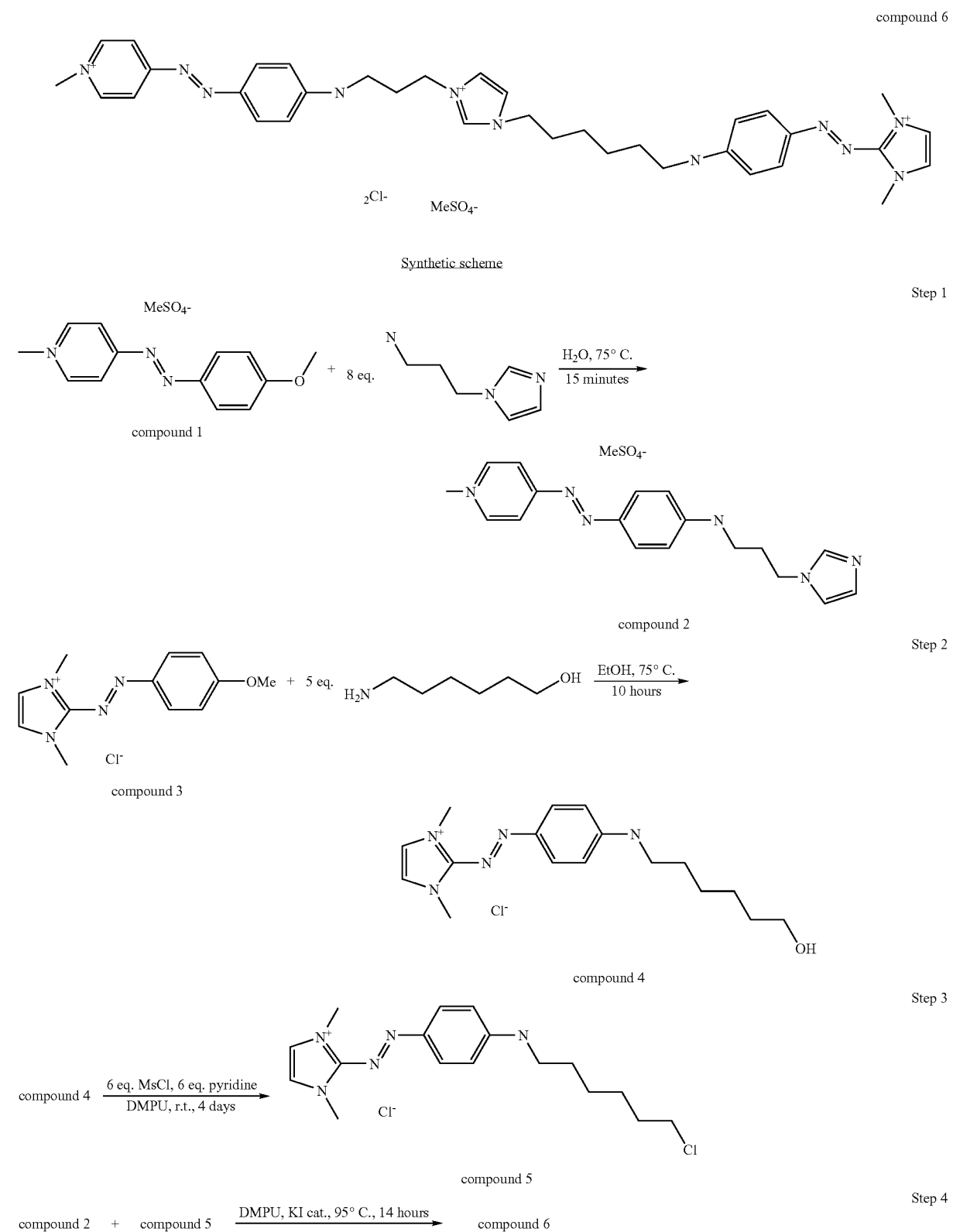

-continued

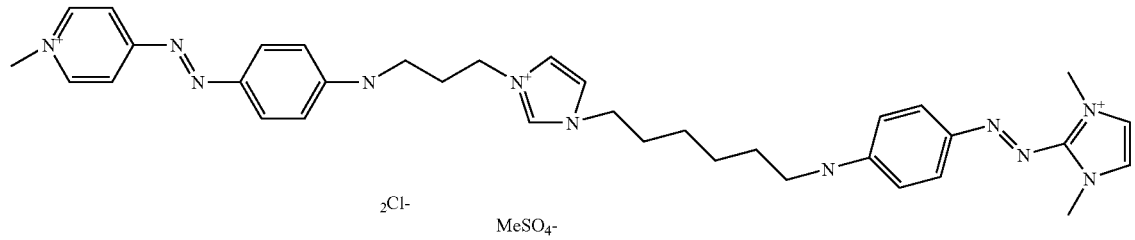

compound 6

Procedure

Step 1

Compound 1 (1 g) was placed in 12 ml of water in a three-necked flask with stirring; 3-aminopropylimidazole (2.8 ml; 8 eq.) was then added to the reaction medium. The mixture was heated to 75° C. (external temperature) with stirring.

After 15 minutes, the heating was stopped and the mixture was allowed to cool to room temperature.

After precipitation of the product from acetone, followed by filtration, compound 2 was recovered. A dark purple-red solid was obtained. The NMR and mass spectra were in accordance with compound 2.

Step 2

Compound 3 (20 g) and ethanol (200 ml) were placed in a three-necked flask and 6-aminohexanol (43.9 g, 5 eq.) was introduced.

The mixture was heated to 70° C. (external temperature) with stirring.

After 10 hours, the heating was stopped and the mixture was allowed to cool to room temperature.

After evaporation of the solvent, compound 4 was recovered.

A red solid was obtained. The NMR and mass spectra were in accordance with compound 4.

Step 3

Compound 4 (3 g), 1,3-dimethyl-3,4,5,6-tetrahydro-2 (1H)-pyrimidinone (80 ml), methanesulfonyl chloride (4 ml, 6 eq.) and pyridine (4.12 ml, 6 eq.) were placed in a three-necked flask.

The mixture was stirred at room temperature for 4 days.

The product was precipitated from ethyl acetate and then filtered off. The precipitate was dissolved in water and then extracted with dichloromethane. The organic phase was dried over sodium sulfate, filtered and then concentrated.

Compound 5 was recovered in the form of a matte-red powder.

The NMR and mass spectra were in accordance with compound 5.

Step 4

Compounds 2 and 5,1,3-dimethyl-3,4,5,6-tetrahydro-2 (1H)-pyrimidinone (4 ml) and a catalytic amount of Kl were placed in a three-necked flask.

The mixture was stirred at 95° C. for 14 hours.

The product was precipitated from ethyl acetate and then filtered. The precipitate was washed several times with dichloromethane. Compound 6 was recovered in the form of a matte dark purple powder.

The NMR and mass spectra show that compound 5 had been synthesized.

Dyeing Example

The composition below was prepared:

| Ingredients | Amount |
|---|---|
| (50/50 C8/C10) Alkyl polyglucoside (2) as a buffered 60% aqueous solution | 12 g |
| Pure absolute ethanol | 20 g |
| Pure benzyl alcohol | 4 g |
| Polyethylene glycol 400 (8 EO) | 6 g |
| Demineralized water | qs 100 g |

$5 \times 10^{-3}$ mol/l of compound 6 were dissolved in the composition described above.

The composition thus obtained was applied to locks of hair containing 90% white hairs.

A fuchsia shade was obtained with compound 6.

EXAMPLE 2

Synthesis of Compound 8:

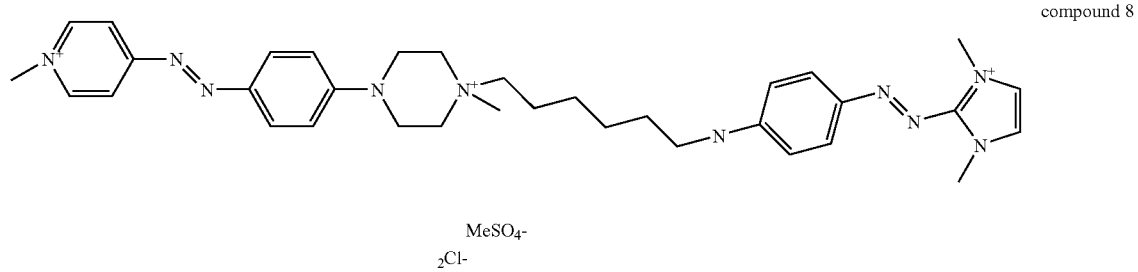

compound 8

Synthetic scheme

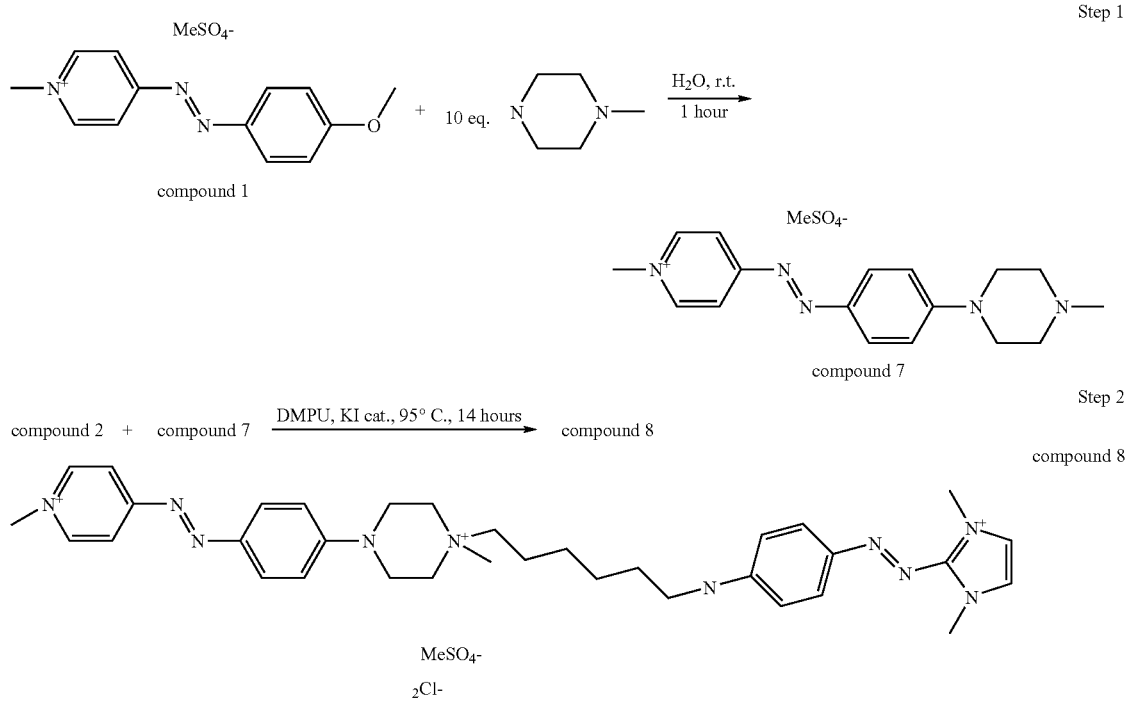

Procedure

Step 1

Compound 1 (1 g) was placed in 10 ml of water in a three-necked flask with stirring; N-methylpiperazine (3.3 ml; 10 eq.) was then added to the reaction medium. The mixture was left at room temperature with stirring.

After 1 hour, the reaction medium was precipitated from 50 ml of acetone.

After filtering off the precipitate, compound 7 was recovered.

A dark violet solid was obtained. The NMR and mass spectra were in accordance with compound 7.

Step 2

Compounds 2 and 7,1,3-dimethyl-3,4,5,6-tetrahydro-2 (1H)-pyrimidinone (4 ml) and a catalytic amount of Kl were placed in a three-necked flask.

The mixture was stirred at 95° C. for 14 hours.

The product was precipitated from ethyl acetate and then filtered off. The precipitate was washed several times with dichloromethane. Compound 8 was recovered in the form of a matte dark purple powder.

Dyeing Example

The process was performed as in example 1.

A strong dark purple shade was obtained with compound 8.

What is claimed is:

1. A cationic compound of formula (I):

Dye1-LK-Dye2         (I)

or the addition salts thereof with an acid, the electrical neutrality of the compound is ensured by at least one cosmetically acceptable anion An, wherein:

Dye1 and Dye2 are such that the compound of formula (I) is not symmetrical, and are chosen from:

Dye1:

Dye2:

wherein:

$W_1$ and $W_6$, which may be identical or different, are each chosen from —$NR_1$— and —O—, wherein $R_1$ is chosen from a hydrogen atom, and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom;

wherein $R_1$ may form with all or part of the group LK and with the nitrogen atom to which each is attached at least one cationic and non-cationic, saturated and unsaturated, aromatic and non-aromatic, optionally substituted 5- to 7-membered heterocycle;

$W'_1$ and $W'_6$, which may be identical or different, are each chosen from —$NR'_1R'_2$ and —$OR'_3$, wherein $R'_1$, $R'_2$ and $R'_3$, which may be identical or different, are each chosen from a hydrogen atom and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom; $R'_1$ and $R'_2$ optionally forming, with the nitrogen atom to which they are attached, an optionally substituted 5- or 7-membered heterocycle optionally comprising another nitrogen or non-nitrogen hetero atom;

wherein $R'_1$, $R'_2$ and $R'_3$, together or separately, may form, with all or part of the group LK and with the nitrogen or oxygen atom to which each is attached, at least one cationic and-non-cationic, saturated and unsaturated, aromatic and non-aromatic, optionally substituted 5- to 7-membered heterocycle;

$W_2$, $W_5$, $W'_2$ and $W'_5$, which may be identical or different, are each chosen from:

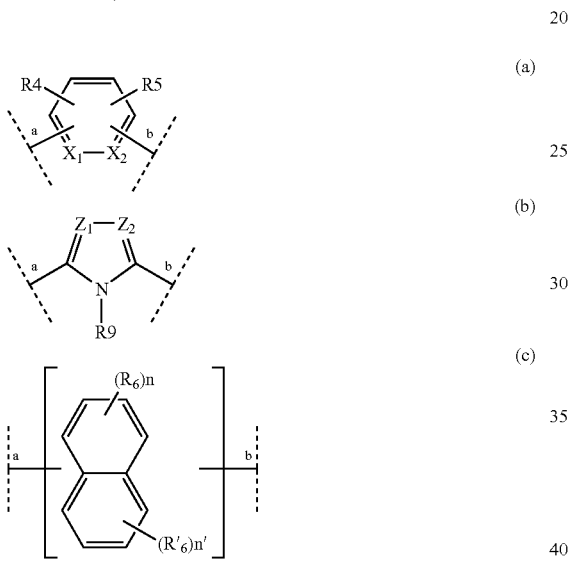

wherein:

$X_1$ is chosen from a nitrogen atom and $CR_7$;
$X_2$ is chosen from a nitrogen atom and $CR_8$;
$Z_1$ is chosen from a nitrogen atom and $CR_{10}$;
$Z_2$ is chosen from a nitrogen atom and $CR_{11}$;
$R_4$, $R_5$, $R_6$, $R'_6$, $R_7$, $R_8$, $R_{10}$ and $R_{11}$, which may be identical or different, are chosen from:
a hydrogen atom
linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom;
a hydroxyl group,
a $C_1$-$C_4$ alkoxy group, a $C_2$-$C_4$ (poly)hydroxyalkoxy group; an alkoxycarbonyl group (RO—CO—) wherein R is chosen from a $C_1$-$C_4$ alkyl radical, and an alkylcarbonyloxy radical (RCO—O—) wherein R is chosen from a $C_1$-$C_4$ alkyl radical;
an amino group, an amino group substituted with at least one $C_1$-$C_4$ alkyl radicals, which may be identical or different, optionally bearing at least one hydroxyl group, the at least one alkyl radical optionally forming, with the nitrogen atom to which it is attached, a 5- or 6-membered heterocycle optionally bearing another nitrogen or non-nitrogen hetero atom; an alkylcarbonylamino group (RCO—NR—) wherein R, which may be identical or different, are each chosen from a $C_1$-$C_4$ alkyl radical; a carbamoyl group ((R)$_2$N—CO) wherein R, which may be identical or different, are chosen from a hydrogen atom and a $C_1$-$C_4$ alkyl radical; a ureido group (N(R)$_2$—CO—NR'—) wherein R and R', which may be identical or different, are each chosen from a hydrogen atom and a $C_1$-$C_4$ alkyl radical; a sulfonamide group ((R)$_2$N—SO$_2$—) wherein R, which may be identical or different, are each chosen from a hydrogen atom and a $C_1$-$C_4$ alkyl radical; an alkylsulfonylamino group (RSO$_2$—NR'—) wherein R and R', which may be identical or different, are each chosen from a hydrogen atom and a $C_1$-$C_4$ alkyl radical; a guanidinium group ((R')$_2$N—C(=NH$_2^+$)—NR—) wherein R and R', which may be identical or different, are each chosen from a hydrogen atom and a $C_1$-$C_4$ alkyl radical;

a nitro group; a cyano group; a halogen atom;

$R_4$, $R_5$, $R_6$, $R'_6$, $R_7$, $R_8$, $R_{10}$ and $R_{11}$, which may be identical or different, may optionally form, with all or some of the groups $W'_1$ or $W'_6$, saturated and unsaturated, aromatic and non-aromatic, optionally substituted 5- to 7-membered heterocycles;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:
a hydrogen atom,
linear and branched, saturated and unsaturated, aromatic and non-aromatic, optionally substituted $C_1$-$C_{16}$ hydrocarbon-based chains, which may form at least one optionally substituted 3- to 7-membered carbon-based ring, n and n', which may be identical or different, are chosen from integers, wherein their sum is less than or equal to 6;

$W_3$ and $W_4$, which may be identical or different, are each chosen from cationic heteroaromatic radicals chosen from:

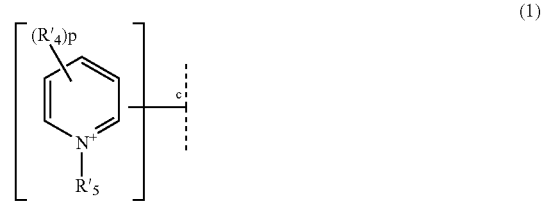

-continued

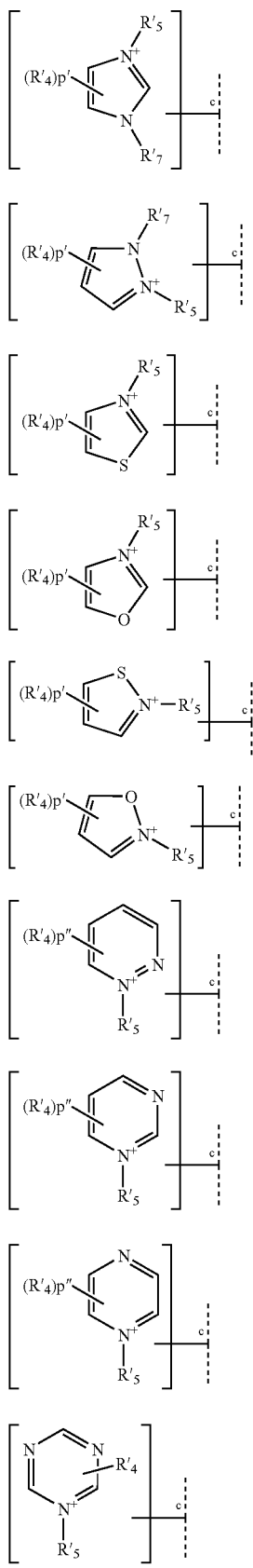

wherein R'$_4$, which may be identical or different, are chosen from:
linear and branched, saturated and unsaturated, aromatic and non-aromatic, optionally substituted C$_1$-C$_{16}$ hydrocarbon-based chains, which may form at least one 3- to 6-membered carbon-based ring, optionally interrupted with at least one hetero atom or with at least one group bearing at least one hetero atom;
a hydroxyl group,
a C$_1$-C$_4$ alkoxy group a C$_2$-C$_4$ (poly)hydroxyalkoxy group; an alkoxycarbonyl group (RO—CO—) wherein R is chosen from a C$_1$-C$_4$ alkyl radical and an alkylcarbonyloxy radical (RCO—O—) wherein R is chosen from a C$_1$-C$_4$ alkyl radical;
an amino group; an amino group substituted with at least one C$_1$-C$_4$ alkyl radical, which may be identical or different, optionally bearing at least one hydroxyl group, the at least one alkyl radical optionally forming, with the nitrogen atom to which they are attached, a 5- or 6-membered heterocycle optionally bearing another nitrogen or non-nitrogen hetero atom; an alkylcarbonylamino group (RCO—NR'—) wherein R is chosen from a C$_1$-C$_4$ alkyl radical and R' is chosen from a hydrogen atom and a C$_1$-C$_4$ alkyl radical; a carbamoyl group ((R)$_2$N—CO—) wherein R, which may be identical or different, are chosen from a hydrogen atom or a C$_1$-C$_4$ alkyl radical; a ureido group (N(R)$_2$—CO—NR'—) wherein R and R', which may be identical or different, are each chosen from a hydrogen atom and a C$_1$-C$_4$ alkyl radical; a sulfonamide group ((R)$_2$N—SO$_2$—) wherein R, which may be identical or different, are each chosen from a hydrogen atom and a C$_1$-C$_4$ alkyl radical; an alkylsulfonylamino group (RSO$_2$—NR'—) wherein R and R', which may be identical or different, are each chosen from a hydrogen atom and a C$_1$-C$_4$ alkyl radical;a guanidinium group ((R')$_2$N—C(=NH$_2^+$)—NR—) wherein R and R', which may be identical or different, are each chosen from a hydrogen atom and a C$_1$-C$_4$ alkyl radical;
a nitro group; a cyano group; a halogen atom;
wherein two radicals R'$_4$ borne by two adjacent carbon atoms of a main ring may optionally form an aromatic or non-aromatic, 5- or 6-membered secondary ring, optionally substituted with at least one group chosen from a hydrogen atom; hydroxyl groups; C$_1$-C$_4$ alkyl radicals; C$_1$-C$_4$ alkoxy radicals; C$_2$-C$_4$(poly)hydroxyalkoxy radicals; amino radicals; amino radicals substituted with at least one C$_1$-C$_4$ alkyl radical, which may be identical or different, optionally bearing at least one hydroxyl group;
R'$_5$ is chosen from linear and branched, saturated and unsaturated, aromatic and non-aromatic, optionally substituted C$_1$-C$_{16}$ hydrocarbon-based chains, which may form at least one optionally substituted 3- to 6-membered carbon-based ring, optionally interrupted with at least one hetero atom or with at least one group bearing at least one hetero atom; wherein R'$_5$ is such that the atom directly linked to the quaternized nitrogen atom is a carbon atom;

R'$_7$ is chosen from an optionally substituted C$_1$-C$_4$ alkyl radical; an optionally substituted phenyl radical; and an optionally substituted benzyl radical;

the bond c links the cationic radical defined by formulae (1) to (11) to the azo group; wherein said bond may be on the main or secondary ring;

p is an number ranging from 0 to 4, p' is an number ranging from 0 to 2 and p" is an number ranging from 0 to 3;

wherein the main ring does not bear the maximum number of substituents, each unsubstituted position bears a nitrogen atom;

LK is chosen from saturated and unsaturated, linear and branched, cyclic and non-cyclic, aromatic and non-aromatic, optionally substituted C$_2$-C$_{40}$ hydrocarbon-based chains, bearing at least one cationic charge, optionally interrupted with at least one hetero atom or group comprising at least one hetero atom;

wherein LK may end with a hetero atom or group bearing at least one hetero atom if LK is linked to W'$_2$ or W'$_5$; and wherein LK may end with a group bearing at least one hetero atom chosen from —CO— and —SO$_2$— if LK is linked to W$_6$ or W$_1$.

2. A compound according to claim 1, wherein R$_1$, R'$_1$, R'$_2$ and R'$_3$, which may be identical or different, are chosen from:

a hydrogen atom;

optionally substituted C$_1$-C$_6$ alkyl radicals;

aryl and arylalkyl radicals, wherein the aryl is optionally substituted;

wherein R$_1$ may form with all or part of the group LK and with the nitrogen atom to which each is attached, a saturated and unsaturated, aromatic and non-aromatic, optionally substituted 5- to 7-membered heterocycle;

wherein R'$_1$, R'$_2$ or R'$_3$, together or separately, may form, with all or part of the group LK and with the nitrogen or oxygen atom to which each is attached, a saturated and unsaturated, aromatic and non-aromatic, optionally substituted 5- to 7-membered heterocycle.

3. A compound according to claim 2, wherein the aryl and arylalkyl radicals, wherein the aryl is optionally substituted is chosen from phenyl and benzyl.

4. A compound according to claim 2, wherein R$_1$, R'$_1$, R'$_2$ and R'$_3$, which may be identical or different, are chosen from:

a hydrogen atom;

optionally substituted C$_1$-C$_3$ alkyl radicals;

a phenyl radical, optionally substituted with at least one radical chosen from hydroxyl, C$_1$-C$_2$ alkoxy; and amino radicals and amino radicals substituted with at least one C$_1$-C$_4$ group optionally bearing at least one hydroxyl group;

wherein R$_1$ or R'$_2$ and R'$_3$, together or separately, may form, with the nitrogen, or oxygen atom for R'$_3$, to which each is attached and all or part of the group LK, a 5- to 7-membered heterocycle chosen from pyrrolidines, piperidines, piperazines and homopiperazines optionally substituted with at least one radical chosen from methyl, hydroxyl, amino and (di)methylamino radicals.

5. A compound according to claim 4, wherein the optionally substituted C$_1$-C$_3$ alkyl radical is chosen from methyl, ethyl 2-hydroxyethyl or 2-methoxyethyl.

6. A compound according to claim 1, wherein R$_1$, R'$_1$, R'$_2$ and R'$_3$, which may be identical or different, are chosen from:

a hydrogen atom;

methyl, ethyl or 2-hydroxyethyl radicals; and a phenyl radical, optionally substituted with radicals chosen from hydroxyl, methoxy, amino, (di)methylamino and (di)(2-hydroxyethyl)amino radicals;

wherein R$_1$ or R'$_2$ and R'$_3$, together or separately, may form, with the nitrogen, or oxygen atom for R'$_3$, to which each is attached and all or part of the group LK, a 5- to 7-membered heterocycle chosen from pyrrolidine, 3-hydroxypyrrolidine, 3-dimethylaminopyrrolidine, piperidine, 2-(2-hydroxyethylpiperidine), 4-(aminomethyl)piperidine, 4-(2-hydroxyethyl)piperidine, 4-(dimethylamino)-piperidine, piperazine, 1-methylpiperazine, 1-(2-hydroxyethyl)piperazine, 1-(2-aminoethyl)piperazine, 1-hydroxyethylethoxypiperazine, homopiperazine and 1-methyl-1,4-perhydrodiazepine.

7. A compound according to claim 1, wherein R$_4$, R$_5$, R$_6$, R'$_6$, R$_7$, R$_8$, R$_{10}$ and R$_{11}$, which may be identical or different, are chosen from:

a hydrogen atom for R$_4$, R$_5$, R$_7$, R$_8$, R$_{10}$ and R$_{11}$;

an optionally substituted C$_1$-C$_{16}$ alkyl radical;

a halogen atom;

a hydroxyl group;

a C$_1$-C$_2$ alkoxy radical; a C$_2$-C$_4$ (poly)hydroxyalkoxy radical;

an amino radical; an amino radical substituted with one or two C$_1$-C$_4$ alkyl radicals, which may be identical or different, optionally bearing at least one group chosen from hydroxyl and C$_1$-C$_4$ dialkylamino groups;

an alkylcarbonylamino radical (RCO—NR'—) wherein R is chosen from a C$_1$-C$_4$ alkyl radical and R' is chosen from a hydrogen and a C$_1$-C$_4$ alkyl radical; a carbamoyl radical ((R)$_2$N—CO—) wherein R, which may be identical or different, are each chosen from a hydrogen atom and a C$_1$-C$_4$ alkyl radical optionally bearing at least one hydroxyl group; an alkylsulfonylamino radical (R'SO$_2$—NR—) wherein R is chosen from a hydrogen atom and a C$_1$-C$_4$ alkyl radical optionally bearing at least one hydroxyl group, and R' is chosen from a C$_1$-C$_4$ alkyl radical; an aminosulfonyl radical ((R)$_2$N—SO$_2$—) wherein R, which may be identical or different, are each chosen from a hydrogen atom and a C$_1$-C$_4$ alkyl radical optionally bearing at least one hydroxyl group; and a bond from W'$_2$ to W'$_1$ or to the group LK, or from W'$_5$ to W'$_6$ or to the group LK.

8. A compound according to claim 1, wherein R$_4$, R$_5$, R$_6$, R'$_6$, R$_7$, R$_8$, R$_{10}$ and R$_{11}$, which may be identical or different, are chosen from:

a hydrogen atom for R$_4$, R$_5$, R$_6$, R'$_6$, R$_7$, R$_8$, R$_{10}$ and R$_{11}$;

a C$_1$-C$_4$ alkyl radical optionally substituted with at least one radical chosen from hydroxyl and acylamino radicals, or amino radicals substituted with two identical or different C$_1$-C$_2$ alkyl radicals, optionally bearing at least one hydroxyl group, or a C$_1$-C$_2$ alkoxy radical;

an amino radical; an amino radical substituted with one or two identical or different C$_1$-C$_2$ alkyl radicals, optionally bearing at least one hydroxyl group; an acylamino radical; a carbamoyl radical; a sulfonylamino radical;

a hydroxyl radical; a C$_1$-C$_2$ alkoxy radical; and bonds from W'$_2$ to W'$_1$ or to the group LK, or from W'$_5$ to W'$_6$ or to the group LK.

9. A compound according to claim 1, wherein R$_9$ is chosen from a hydrogen atom; a C$_1$-C$_{15}$ alkyl radical; a C$_2$-C$_6$ monohydroxyalkyl radical; a C$_2$-C$_6$-polyhydroxyalkyl radical; a (C$_1$-C$_6$)alkoxy(C$_2$-C$_6$)alkyl radical; an optionally substituted aryl radical; an optionally substituted arylalkyl radical; a C$_2$-C$_6$ aminoalkyl radical; and a C$_2$-C$_6$ aminoalkyl radical, the amine of which is substituted with two identical or different, optionally substituted C$_1$-C$_4$ alkyl radicals;

wherein R$_9$ is such that the atom directly linked to the nitrogen atom is a carbon atom.

10. A compound according to claim 9, wherein R$_9$ is chosen from a hydrogen atom; a C$_1$-C$_6$ alkyl radical; a C$_2$-C$_6$ monohydroxyalkyl radical; a C$_2$-C$_6$ polyhydroxyalkyl radical; a (C$_1$-C$_6$)alkoxy(C$_2$-C$_6$)alkyl radical; a phenyl radical optionally substituted with a group chosen from at least one chlorine atom, a hydroxyl group, a group RCO—NH— wherein R is chosen from a C$_1$-C$_4$ alkyl radical and an amino radical substituted with two identical or different C$_1$-C$_4$ alkyl radicals; a benzyl radical; a C$_1$-C$_6$ aminoalkyl radical; and a C$_1$-C$_6$ aminoalkyl radical wherein the amine is substituted with two identical or different C$_1$-C$_4$ alkyl radicals;

wherein R$_9$ is such that the atom directly linked to the nitrogen atom is a carbon atom.

11. A compound according to claim 1, wherein W$_2$, W$_5$, W'$_2$ and W'$_5$, which may be identical or different, are each chosen from compound of formula (a) or (c).

12. A compound according to claim 1, wherein X$_1$ is chosen from CR$_7$.

13. A compound according to claim 1, wherein X$_2$ is chosen from CR$_8$.

14. A compound according to claim 1, wherein W$_3$ and W$_4$, which may be identical or different, are each chosen from:

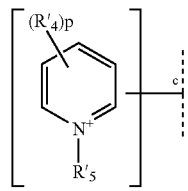

(1)

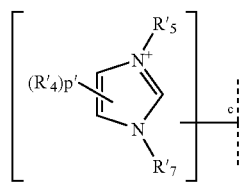

(2)

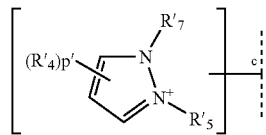

(3)

wherein R'$_4$, R'$_5$, R'$_7$, p, p' and c are as defined in claim 1.

15. A compound according to claim 14, wherein the aromatic heterocycle is chosen from 2-imidazolium, 2-benzimidazolium, 2-pyridinium, 3-pyridinium, 4-pyridinium, 2-quinolinium, 4-quinolinium, 3-pyrazolium, 4-pyrazolium, 3-indazolium, 4-indazolium, 5-indazolium, 6-indazolium and 7-indazolium;

wherein at least one of the two groups W$_3$ or W$_4$ is not chosen from an unsubstituted imidazolium group.

16. A compound according to claim 1, wherein LK is chosen from the following formula:

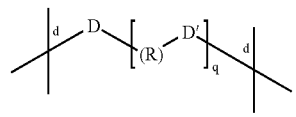

wherein

D and D', which may be identical or different, are each chosen from linear and branched, saturated and unsaturated C$_1$-C$_{14}$ hydrocarbon-based groups, optionally interrupted with at least one hetero atom or with at least one group bearing at least one hetero atom;

the bond d links the arms D and D' to the groups W$_1$, W$_6$, W'$_2$ and W'$_5$;

q is greater than or equal to 1;

R is chosen from

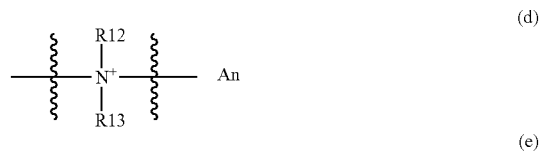

(d)

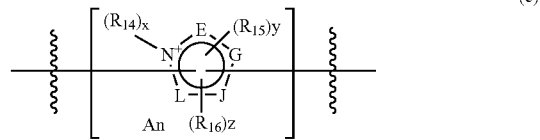

(e)

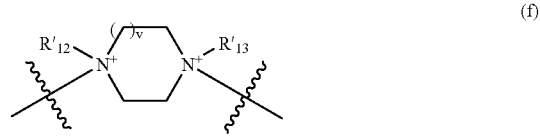

(f)

wherein

R$_{12}$, R$_{13}$, R'$_{12}$ and R'$_{13}$, which may be identical or different, are each chosen from a C$_1$-C$_{15}$ alkyl radical; a C$_1$-C$_6$ monohydroxyalkyl radical; a C$_2$-C$_6$ polyhydroxyalkyl radical; a (C$_1$-C$_6$)alkoxy(C$_1$-C$_6$)alkyl radical; an aryl radical; an arylalkyl radical; a C$_1$-C$_6$ amidoalkyl radical; a C$_1$-C$_6$ aminoalkyl radical; and a C$_1$-C$_6$ aminoalkyl radical wherein the amine is substituted with at least one group, which may be identical or different, chosen from C$_1$-C$_4$ alkyl, (C$_1$-C$_6$)alkylcarbonyl, acylamino and (C$_1$-C$_6$)alkylsulfonyl radicals;

R$_{12}$ and R$_{13}$ may form, together with the nitrogen atom to which they are attached, a 5-, 6- or 7-membered saturated cationic ring that may comprise at least one hetero atom, the cationic ring optionally is substituted with group chosen from a halogen atom, a hydroxyl radical, a C$_1$-C$_6$ alkyl radical, a C$_1$-C$_6$ monohydroxyalkyl radical, a C$_2$-C$_6$ polyhydroxyalkyl radical, a C$_1$-C$_6$ alkoxy radical, an amido radical, a (C$_1$-C$_6$) alkylcarbonyl radical, a thio radical, a C$_1$-C$_6$ thioalkyl radical, a (C$_1$-C$_6$)alkylthio radical, an amino radical and an amino radical substituted with at least one group, which may be identical or different, chosen from C$_1$-C$_6$ alkyl, (C$_1$-C$_6$)alkylcarbonyl, acylamino or (C$_1$-C$_6$)alkylsulfonyl radicals;

R$_{12}$ or R$_{13}$ may form, with D or D', a 5-, 6- or 7-membered saturated cationic ring that may comprise at least one hetero atom, the cationic ring optionally is substituted with a group chosen from a halogen atom, a hydroxyl radical, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a $(C_1$-$C_6)$ alkylcarbonyl radical, a thio radical, a $C_1$-$C_6$ thioalkyl radical, a $(C_1$-$C_6)$alkylthio radical, an amino radical and an amino radical substituted with at least one group, which may be identical or different, chosen from $C_1$-$C_6$ alkyl, $(C_1$-$C_6)$alkylcarbonyl, acylamino or $(C_1$-$C_6)$alkylsulfonyl radicals;

$R_{12}$ and $R_{13}$ may form with $W_1$ or $W_6$ a 5-, 6- or 7-membered, saturated and unsaturated, aromatic and non-aromatic, optionally substituted cationic heterocycle;

the ring members E, G, J and L, which may be identical or different, are each chosen from carbon, oxygen, sulfur or nitrogen atom to form a ring chosen from pyrazolium, imidazolium, triazolium, oxazolium, isoxazolium, thiazolium or isothiazolium rings, $R_{14}$ has the same meaning as $R_{12}$;

$R_{15}$ is chosen from a $C_1$-$C_6$ alkyl radical; a $C_1$-$C_6$ monohydroxyalkyl radical, a $C_2$-$C_6$ polyhydroxyalkyl radical, a $(C_1$-$C_6)$alkoxy$(C_1$-$C_6)$alkyl radical, a $C_2$-$C_6$ carbamylalkyl radical, a $(C_1$-$C_6)$alkylcarboxy$(C_1$-$C_6)$alkyl radical and a benzyl radical; wherein $R_{15}$ is attached to a nitrogen atom, $R_{16}$, which may be identical or different, are each chosen from a hydrogen atom, halogen atom, a $C_1$-$C_6$ alkyl radical, a $C_1$-$C_6$ monohydroxyalkyl radical, a $C_2$-$C_6$ polyhydroxyalkyl radical, a $C_1$-$C_6$ alkoxy radical, an amido radical, a carboxyl radical, a $C_1$-$C_6$ alkylcarbonyl radical, a $C_1$-$C_6$ thioalkyl radical, a $(C_1$-$C_6)$alkylthio radical, an amino radical disubstituted with a $(C_1$-$C_6)$alkyl, $(C_1$-$C_6)$alkylcarbonyl or $(C_1$-$C_6)$alkylsulfonyl radical, a benzyl radical, and a phenyl radical optionally substituted with at least one radicals chosen from methyl, hydroxyl, amino and methoxy radicals, wherein $R_{16}$ is attached to a carbon atom, An is chosen from an organic or mineral anion;

z is a number ranging from 1 to 3;

y is a number ranging from 0 to 1;

v is a number ranging from 1 to 2;

x is a number ranging from 0 to 1;
when x=0, then one of the linker arms D or D' is attached to the quaternized nitrogen atom, and
when x=1, at least one of the linker arms D and/or D' is attached to a carbon atom.

17. A compound according to claim 16, wherein q is equal to 1 or 2.

18. A compound according to claim 16, wherein, in formula (d), $R_{12}$ and $R_{13}$, which may be identical or different, are chosen from a $C_1$-$C_6$ alkyl radical, a $C_1$-$C_4$ monohydroxyalkyl radical, a $C_2$-$C_4$ polyhydroxyalkyl radical, a $(C_1$-$C_6)$alkoxy$(C_2$-$C_4)$alkyl radical, a $C_2$-$C_6$ amidoalkyl radical and a $C_2$-$C_6$ dimethylaminoalkyl radical.

19. A compound according to claim 18, wherein D and D', which may be identical or different, are chosen from a $C_1$-$C_6$ alkyl chain that is optionally substituted.

20. A compound according to claim 16, wherein, in formula (e), the ring members E, G, J and L form a ring chosen from imidazolium, pyrazolium, oxazolium or thiazolium rings; and wherein x and b are equal to 0.

21. A compound according to claim 20, wherein D and D', which may be identical or different, are each chosen from a $C_1$-$C_4$ alkyl chain that may be substituted.

22. A compound according to claim 20, wherein $R_{14}$ is chosen from a methyl, ethyl or 2-hydroxyethyl radical.

23. A compound according to claim 16, wherein, in formula (f), $R'_{12}$ and $R'_{13}$, which may be identical or different, are chosen from a $C_1$-$C_6$ alkyl radical, a $C_1$-$C_4$ monohydroxyalkyl radical, a $C_2$-$C_4$ polyhydroxyalkyl radical, a $(C_1$-$C_6)$alkoxy$(C_2$-$C_4)$alkyl radical, a $C_2$-$C_6$ amidoalkyl radical and a $C_2$-$C_6$ dimethylaminoalkyl radical.

24. A compound according to claim 23, wherein D and D', which may be identical or different, are chosen from a $C_1$-$C_6$ alkyl chain that may be substituted.

25. A compound according to claim 16, wherein the coefficient v is equal to 1.

26. A compound according to claim 1, wherein the formula (I) compounds are chosen from:

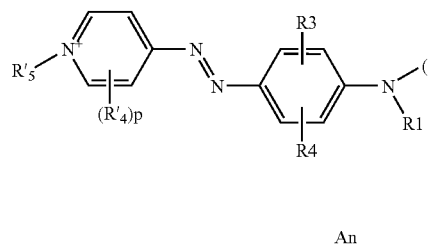

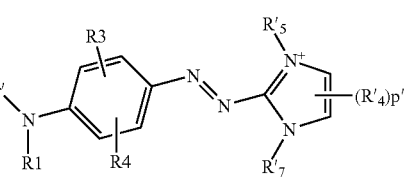

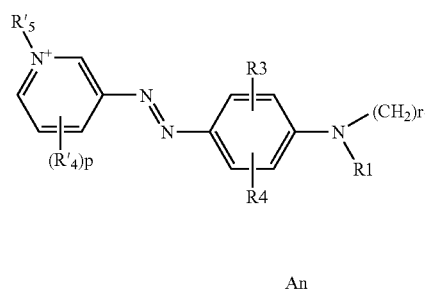

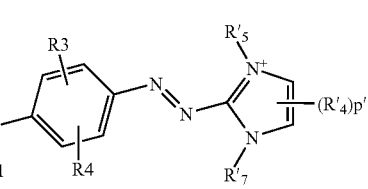

-continued
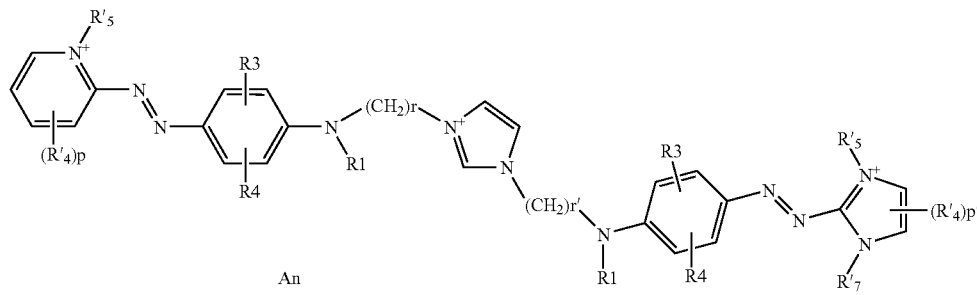
An
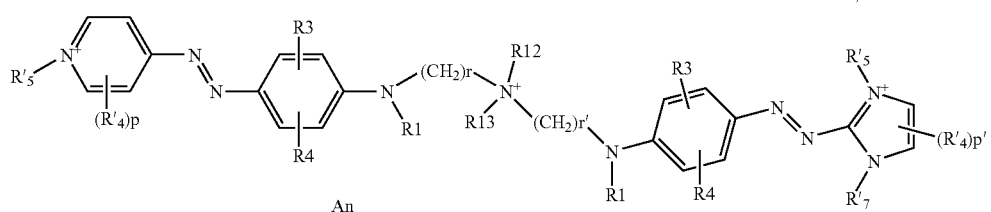
An
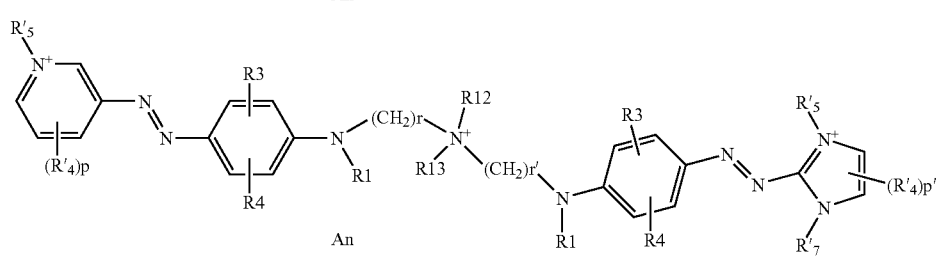
An
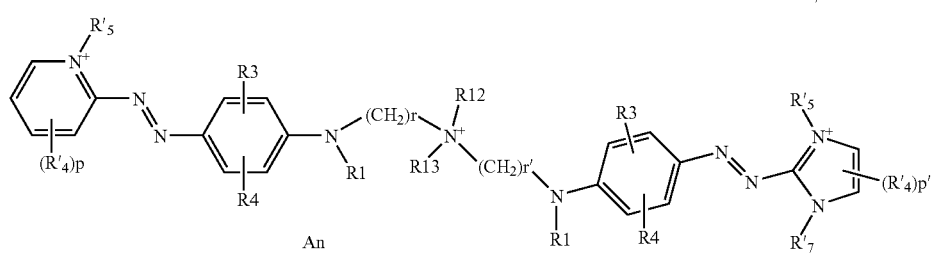
An
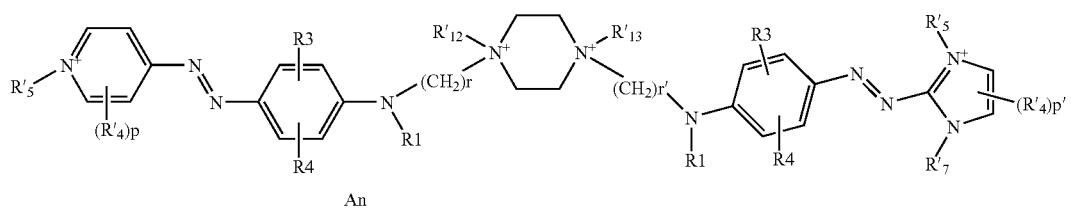
An
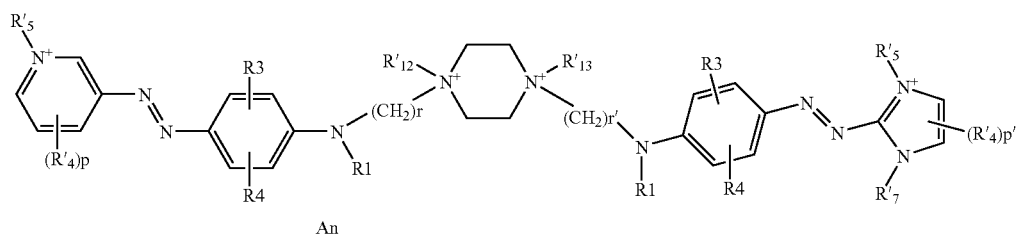
An
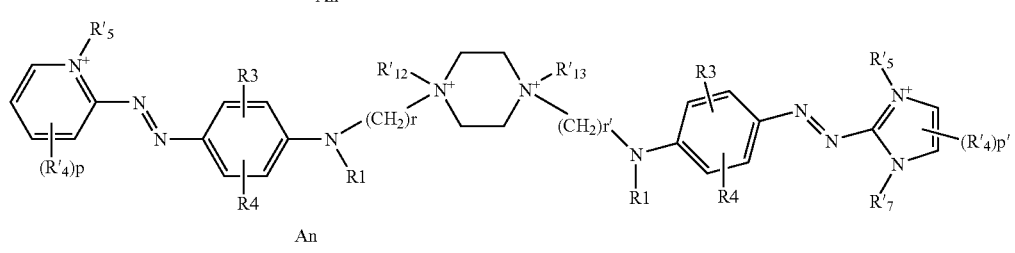
An -continued

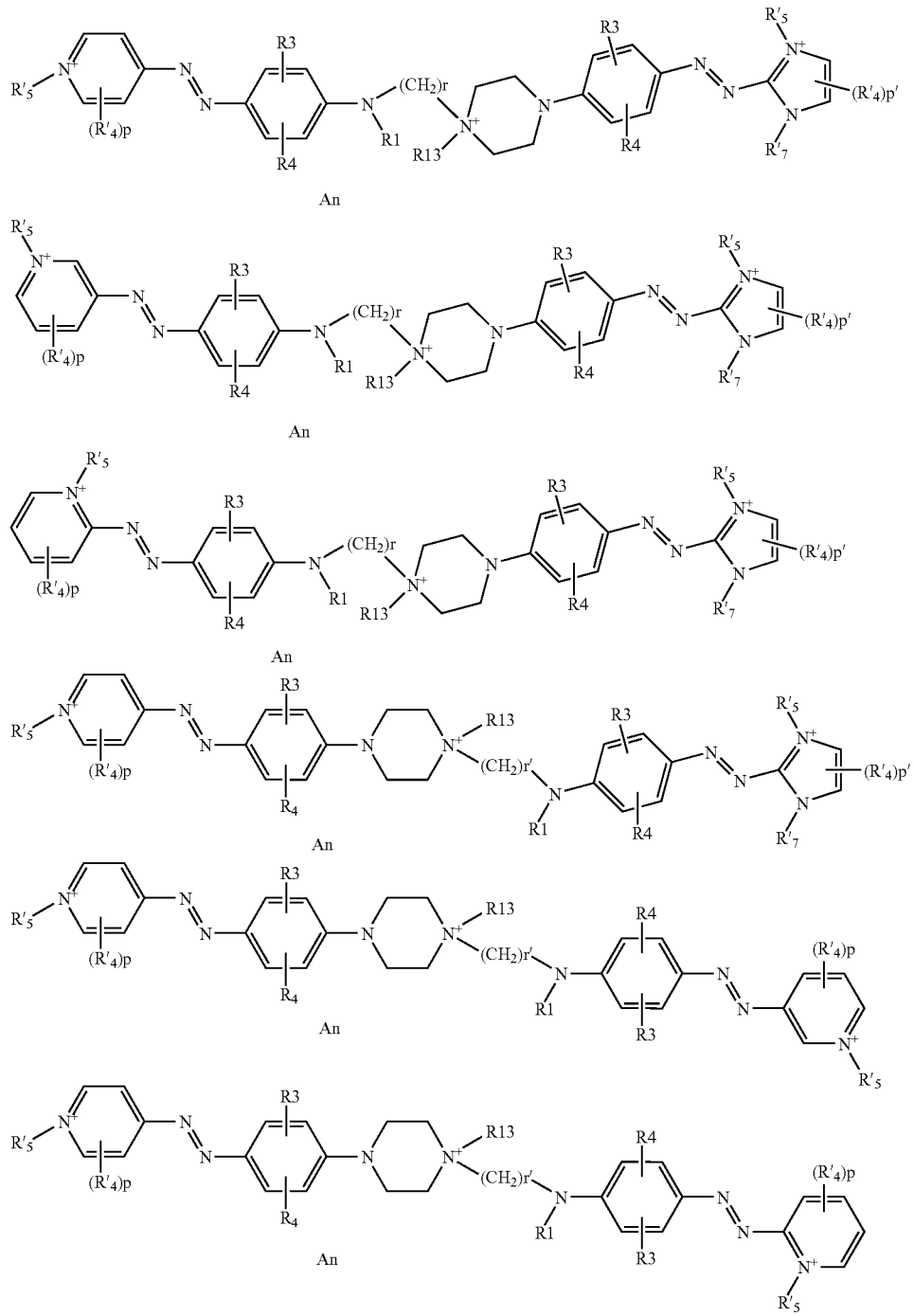

wherein:
R$_1$, R$_3$, R$_4$, R$_{12}$, R$_{13}$, R'$_4$, R'$_5$, R'$_7$, R'$_{12}$, R'$_{13}$, p and p' are as defined in claim 1;
r and r', which may be identical or different, are numbers ranging from 1 to 10;
wherein the electrical neutrality of the molecule is respected by the presence of at least one cosmetically acceptable anion An, as defined in claim 1.

27. A compound according to claim 1, wherein the cosmetically acceptable anion is chosen from halides; hydroxides; sulfates; hydrogen sulfates; (C$_1$-C$_6$)alkyl sulfates; phosphates; carbonates; hydrogen carbonates; perchlorates; acetates; tartrates; citrates; oxalates; (C$_1$-C$_6$)alkylsulfonates; arylsulfonates, which are unsubstituted or substituted with a C$_1$-C$_4$ alkyl radical.

28. A compound according to claim 27, wherein the arylsulfonate is 4-tolylsulfonate.

29. A dye composition comprising, in a medium that is suitable for dyeing keratin fibers, as direct dye, at least one compound of formula (I):

Dye1-LK-Dye2       (I)

or the addition salts thereof with an acid, the electrical neutrality of the compound is ensured by at least one cosmetically acceptable anion An, wherein:

Dye1 and Dye2 are such that the compound of formula (I) is not symmetrical, and are chosen from:

Dye1:

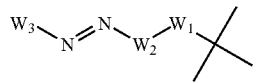 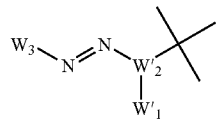

Dye2:

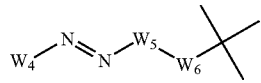 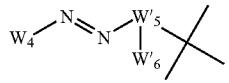

wherein:
- $W_1$ and $W_6$, which may be identical or different, are each chosen from $-NR_1-$ and $-O-$, wherein $R_1$ is chosen from a hydrogen atom, and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom;
- wherein $R_1$ may form with all or part of the group LK and with the nitrogen atom to which each is attached at least one cationic and non-cationic, saturated and unsaturated, aromatic and non-aromatic, optionally substituted 5- to 7-membered heterocycle;
- $W'_1$ and $W'_6$, which may be identical or different, are each chosen from $-NR'_1R'_2$ and $-OR'_3$, wherein $R'_1$, $R'_2$ and $R'_3$, which may be identical or different, are each chosen from a hydrogen atom and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom; $R'_1$ and $R'_2$ optionally forming, with the nitrogen atom to which they are attached, an optionally substituted 5- or 7-membered heterocycle optionally comprising another nitrogen or non-nitrogen hetero atom;
- wherein $R'_1$, $R'_2$ and $R'_3$, together or separately, may form, with all or part of the group LK and with the nitrogen or oxygen atom to which each is attached, at least one cationic and non-cationic, saturated and unsaturated, aromatic and non-aromatic, optionally substituted 5- to 7-membered heterocycle;
- $W_2$, $W_5$, $W'_2$ and $W'_5$, which may be identical or different, are each chosen from:

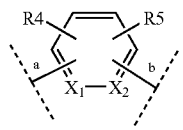

-continued

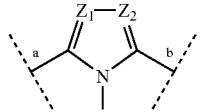

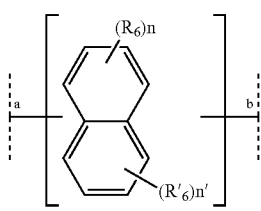

wherein:
- $X_1$ is chosen from a nitrogen atom and $CR_7$;
- $X_2$ is chosen from a nitrogen atom and $CR_8$;
- $Z_1$ is chosen from a nitrogen atom and $CR_{10}$;
- $Z_2$ is chosen from a nitrogen atom and $CR_{11}$;
- $R_4$, $R_5$, $R_6$, $R'_6$, $R_7$, $R_8$, $R_{10}$ and $R_{11}$, which may be identical or different, are chosen from:
  - a hydrogen atom
  - linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom;
  - a hydroxyl group,
  - a $C_1$-$C_4$ alkoxy group, a $C_2$-$C_4$ (poly)hydroxyalkoxy group; an alkoxycarbonyl group (RO—CO—) wherein R is chosen from a $C_1$-$C_4$ alkyl radical, and an alkylcarbonyloxy radical (RCO—O—) wherein R is chosen from a $C_1$-$C_4$ alkyl radical;
  - an amino group, an amino group substituted with at least one $C_1$-$C_4$ alkyl radicals, which may be identical or different, optionally bearing at least one hydroxyl group, the at least one alkyl radical optionally forming, with the nitrogen atom to which it is attached, a 5- or 6-membered heterocycle optionally bearing another nitrogen or non-nitrogen hetero atom; an alkylcarbonylamino group (RCO—NR—) wherein R, which may be identical or different, are each chosen from a $C_1$-$C_4$ alkyl radical; a carbamoyl group $((R)_2N-CO)$ wherein R, which may be identical or different, are chosen from a hydrogen atom and a $C_1$-$C_4$ alkyl radical; a ureido group $(N(R)_2-CO-NR'-)$ wherein R and R', which may be identical or different, are each chosen from a hydrogen atom and a $C_1$-$C_4$ alkyl radical; a sulfonamide group $((R)_2N-SO_2-)$ wherein R, which may be identical or different, are each chosen from a hydrogen atom and a $C_1$-$C_4$ alkyl radical; an alkylsulfonylamino group $(RSO_2-NR'-)$ wherein R and R', which may be identical or different, are each chosen from a hydrogen atom and a $C_1$-$C_4$ alkyl radical; a guanidinium group $((R')_2N-C(=NH_2^+)-NR-)$ wherein R and R', which may be identical or different, are each chosen from a hydrogen atom and a $C_1$-$C_4$ alkyl radical;
a nitro group; a cyano group; a halogen atom;
$R_4$, $R_5$, $R_6$, $R'_6$, $R_7$, $R_8$, $R_{10}$ and $R_{11}$, which may be identical or different, may optionally form, with all or some of the groups $W'_1$ or $W'_6$, saturated and unsaturated, aromatic and non-aromatic, optionally substituted 5- to 7-membered heterocycles;
a bond from $W'_2$ to $W'_1$ or to the group LK, or from $W'_5$ to $W'_6$ or to the group LK;
a is the bond from $W_2$, $W_5$, $W'_2$ or $W'_5$ to the azo group —N=N—;
b is the bond from $W_2$ to $W_1$, from $W_5$ to $W_6$, from $W'_2$ to $W'_1$ or to the group LK, or from $W'_5$ to $W'_6$ or to the group LK;
$R_9$ is chosen from:
a hydrogen atom,
linear and branched, saturated and unsaturated, aromatic and non-aromatic, optionally substituted $C_1$-$C_{16}$ hydrocarbon-based chains, which may form at least one optionally substituted 3- to 7-membered carbon-based ring,
n and n', which may be identical or different, are chosen from integers, wherein their sum is less than or equal to 6;
$W_3$ and $W_4$, which may be identical or different, are each chosen from cationic heteroaromatic radicals chosen from:

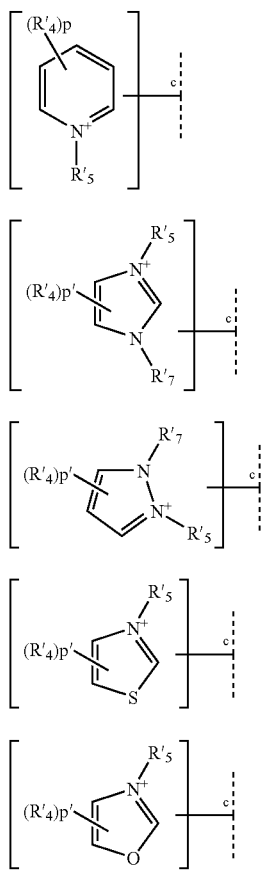

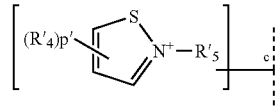

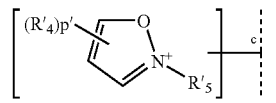

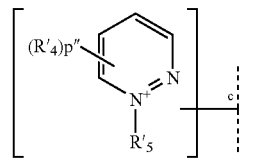

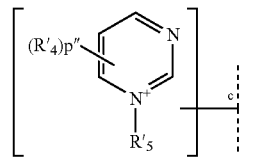

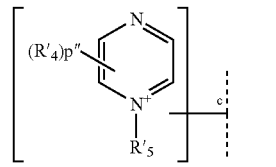

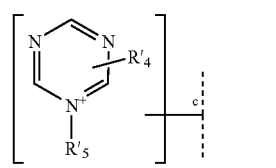

wherein $R'_4$, which may be identical or different, are chosen from:
linear and branched, saturated and unsaturated, aromatic and non-aromatic, optionally substituted $C_1$-$C_{16}$ hydrocarbon-based chains, which may form at least one 3- to 6-membered carbon-based ring, optionally interrupted with at least one hetero atom or with at least one group bearing at least one hetero atom;
a hydroxyl group,
a $C_1$-$C_4$ alkoxy group a $C_2$-$C_4$ (poly)hydroxyalkoxy group; an alkoxycarbonyl group (RO—CO—) wherein R is chosen from a $C_1$-$C_4$ alkyl radical and an alkylcarbonyloxy radical (RCO—O—) wherein R is chosen from a $C_1$-$C_4$ alkyl radical;
an amino group; an amino group substituted with at least one $C_1$-$C_4$ alkyl radical, which may be identical or different, optionally bearing at least one hydroxyl group, the at least one alkyl radical optionally forming, with the nitrogen atom to which they are attached, a 5- or 6-membered heterocycle optionally bearing another nitrogen or non-nitrogen hetero atom; an alkylcarbonylamino group (RCO—NR'—) wherein R is chosen from a $C_1$-$C_4$ alkyl radical and R' is chosen from a hydrogen atom and a $C_1$-$C_4$ alkyl radical; a carbamoyl group ((R)₂N—CO—) wherein R, which may be identical or different, are chosen from a hydrogen atom or a C₁-C₄ alkyl radical; a ureido group (N(R)₂—CO—NR'—) wherein R and R', which may be identical or different, are each chosen from a hydrogen atom and a C₁-C₄ alkyl radical; a sulfonamide group ((R)₂N—SO₂—) wherein R, which may be identical or different, are each chosen from a hydrogen atom and a C₁-C₄ alkyl radical; an alkylsulfonylamino group (RSO₂—NR'—) wherein R and R', which may be identical or different, are each chosen from a hydrogen atom and a C₁-C₄ alkyl radical; a guanidinium group ((R')₂N—C(=NH₂⁺)—NR—) wherein R and R', which may be identical or different, are each chosen from a hydrogen atom and a C₁-C₄ alkyl radical;

a nitro group; a cyano group; a halogen atom;

wherein two radicals R'₄-borne by two adjacent carbon atoms of a main ring may optionally form an aromatic or non-aromatic, 5- or 6-membered secondary ring, optionally substituted with at least one group chosen from a hydrogen atom; hydroxyl groups; C₁-C₄ alkyl radicals; C₁-C₄ alkoxy radicals; C₂-C₄(poly)hydroxyalkoxy radicals; amino radicals; amino radicals substituted with at least one C₁-C₄ alkyl radical, which may be identical or different, optionally bearing at least one hydroxyl group;

R'₅ is chosen from linear and branched, saturated and unsaturated, aromatic and non-aromatic, optionally substituted C₁-C₁₆ hydrocarbon-based chains, which may form at least one optionally-substituted 3- to 6-membered carbon-based ring, optionally interrupted with at least one hetero atom or with at least one group bearing at least one hetero atom; wherein R'₅ is such that the atom directly linked to the quaternized nitrogen atom is a carbon atom;

R'₇ is chosen from an optionally substituted C₁-C₄ alkyl radical; an optionally substituted phenyl radical; and an optionally substituted benzyl radical;

the bond c links the cationic radical defined by formulae (1) to (11) to the azo group; wherein said bond may be on the main or secondary ring;

p is an number ranging from 0 to 4, p' is an number ranging from 0 to 2 and p" is an number ranging from 0 to 3;

wherein the main ring does not bear the maximum number of substituents, each unsubstituted position bears a nitrogen atom;

LK is chosen from saturated and unsaturated, linear and branched, cyclic and non-cyclic, aromatic and non-aromatic, optionally substituted C₂-C₄₀ hydrocarbon-based chains, bearing at least one cationic charge, optionally interrupted with at least one hetero atom or group comprising at least one hetero atom;

wherein LK may end with a hetero atom or group bearing at least one hetero atom if LK is linked to W'₂ or W'₅; and wherein LK may end with a group bearing at least one hetero atom chosen from —CO— and —SO₂— if LK is linked to W₆ or W₁.

30. A composition according to claim 29, wherein the at least one compound of formula (I) is present in an amount ranging from 0.001% to 20% by weight, relative to the total weight of the dye composition.

31. A composition according to claim 30, wherein the at least one compound of formula (I) is present in an amount ranging from 0.01% to 10% by weight, relative to the total weight of the dye composition.

32. A composition according to claim 29, comprising at least one additional direct dye, and at least one oxidation base optionally combined with at least one coupler, or mixtures thereof.

33. A composition according to claim 32, wherein the additional direct dye is a cationic or nonionic dye chosen from nitrobenzene dyes, azo, azomethine, methine, tetraazapentamethine, anthraquinone, naphthoquinone, benzoquinone, phenothiazine, indigoid, xanthene, phenanthridine, phthalocyanin and triarylmethane-based dyes and natural dyes.

34. A composition according to claim 32, wherein the oxidation base is chosen from o-phenylenediamines, p-phenylenediamines, double bases, o-aminophenols, p-aminophenols and heterocyclic bases, the addition salts thereof with an acid.

35. A composition according to claim 32, wherein the coupler is chosen from m-aminophenols, m-phenylenediamines, m-diphenols, naphthols and heterocyclic couplers, the addition salts thereof with an acid, and also mixtures thereof.

36. A composition according to claim 29, wherein it comprises at least one oxidizing agent.

37. A process for dyeing keratin fibers, comprising placing at least one composition comprising, in a medium that is suitable for dyeing keratin fibers, as direct dye, at least one compound of formula (I):

Dye1-LK-Dye2     (I)

or the addition salts thereof with an acid, the electrical neutrality of the compound is ensured by at least one cosmetically acceptable anion An, wherein:

Dye1 and Dye2 are such that the compound of formula (I) is not symmetrical, and are chosen from:

Dye1:

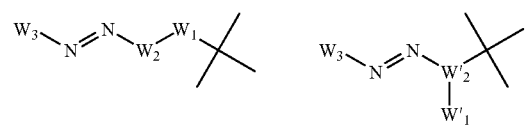

Dye2:

wherein:

W₁ and W₆, which may be identical or different, are each chosen from —NR₁— and —O—, wherein R₁ is chosen from a hydrogen atom, and saturated and unsaturated, aromatic and non-aromatic, optionally substituted C₁-C₂₀ hydrocarbon-based chains, which may form at least one optionally substituted 3- to 7-membered carbon-based ring, optionally interrupted with at least one hetero atom or with at least one group bearing at least one hetero atom;

wherein $R_1$ may form with all or part of the group LK and with the nitrogen atom to which each is attached at least one cationic and non-cationic, saturated and unsaturated, aromatic and non-aromatic, optionally substituted 5- to 7-membered heterocycle;

$W'_1$ and $W'_6$, which may be identical or different, are each chosen from $-NR'_1R'_2$ and $-OR'_3$, wherein $R'_1$, $R'_2$ and $R'_3$, which may be identical or different, are each chosen from a hydrogen atom and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom; $R'_1$ and $R'_2$ optionally forming, with the nitrogen atom to which they are attached, an optionally substituted 5- or 7-membered heterocycle optionally comprising another nitrogen or non-nitrogen hetero atom;

wherein $R'_1$, $R'_2$ and $R'_3$, together or separately, may form, with all or part of the group LK and with the nitrogen or oxygen atom to which each is attached, at least one cationic and non-cationic, saturated and unsaturated, aromatic and non-aromatic, optionally substituted 5- to 7-membered heterocycle;

$W_2$, $W_5$, $W'_2$ and $W'_5$, which may be identical or different, are each chosen from:

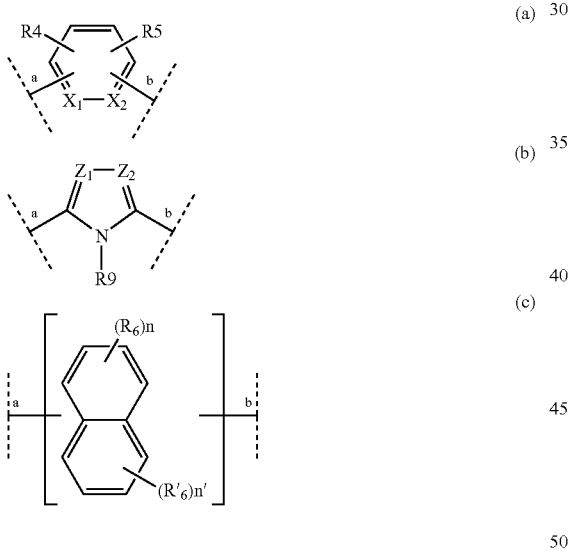

wherein:
$X_1$ is chosen from a nitrogen atom and $CR_7$;
$X_2$ is chosen from a nitrogen atom and $CR_8$;
$Z_1$ is chosen from a nitrogen atom and $CR_{10}$;
$Z_2$ is chosen from a nitrogen atom and $CR_{11}$;
$R_4$, $R_5$, $R_6$, $R'_6$, $-R_7$, $R_8$, $R_{10}$ and $R_{11}$, which may be identical or different, are chosen from:
a hydrogen atom
linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom;

a hydroxyl group,
a $C_1$-$C_4$ alkoxy group, a $C_2$-$C_4$ (poly)hydroxyalkoxy group; an alkoxycarbonyl group (RO—CO—) wherein R is chosen from a $C_1$-$C_4$ alkyl radical, and an alkylcarbonyloxy radical (RCO—O—) wherein R is chosen from a $C_1$-$C_4$ alkyl radical;

an amino group, an amino group substituted with at least one $C_1$-$C_4$ alkyl radicals, which may be identical or different, optionally bearing at least one hydroxyl group, the at least one alkyl radical optionally forming, with the nitrogen atom to which it is attached, a 5- or 6-membered heterocycle optionally bearing another nitrogen or non-nitrogen hetero atom; an alkylcarbonylamino group (RCO—NR—) wherein R, which may be identical or different, are each chosen from a $C_1$-$C_4$ alkyl radical; a carbamoyl group $((R)_2N-CO)$ wherein R, which may be identical or different, are chosen from a hydrogen atom and a $C_1$-$C_4$ alkyl radical; a ureido group $(N(R)_2-CO-NR'-)$ wherein R and R', which may be identical or different, are each chosen from a hydrogen atom and a $C_1$-$C_4$ alkyl radical; a sulfonamide group $((R)_2N-SO_2-)$ wherein R, which may be identical or different, are each chosen from a hydrogen atom and a $C_1$-$C_4$ alkyl radical; an alkylsulfonylamino group $(RSO_2-NR'-)$ wherein R and R', which may be identical or different, are each chosen from a hydrogen atom and a $C_1$-$C_4$ alkyl radical; a guanidinium group $((R')_2N-C(=NH_2^+)-NR-)$ wherein R and R', which may be identical or different, are each chosen from a hydrogen atom and a $C_1$-$C_4$ alkyl radical;

a nitro group; a cyano group; a halogen atom;

$R_4$, $R_5$, $R_6$, $R'_6$, $R_7$, $R_8$, $R_{10}$ and $R_{11}$, which may be identical or different, may optionally form, with all or some of the groups $W'_1$ or $W'_6$, saturated and unsaturated, aromatic and non-aromatic, optionally substituted 5- to 7-membered heterocycles;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group $-N=N-$;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:
a hydrogen atom,
linear and branched, saturated and unsaturated, aromatic and non-aromatic, optionally substituted $C_1$-$C_{16}$ hydrocarbon-based chains, which may form at least one optionally substituted 3- to 7-membered carbon-based ring, n and n', which may be identical or different, are chosen from integers, wherein their sum is less than or equal to 6;

$W_3$ and $W_4$, which may be identical or different, are each chosen from cationic heteroaromatic radicals chosen from:

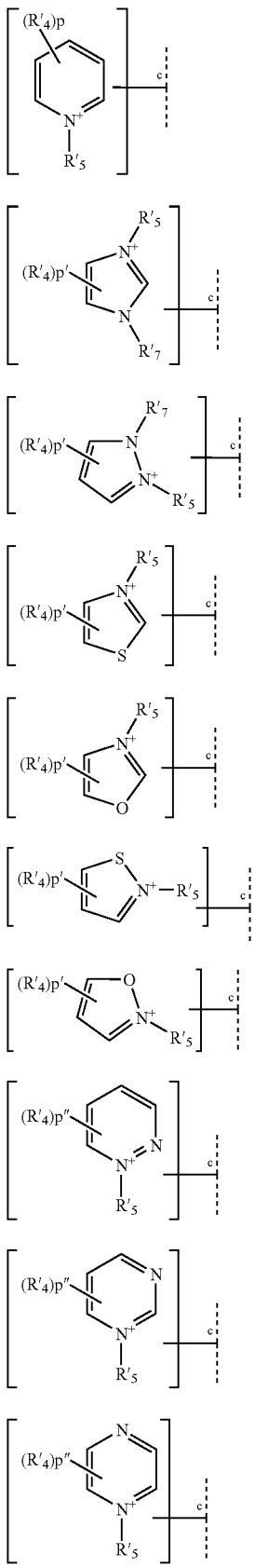

(1)

(2)

(3)

(4)

(5)

(6)

(7)

(8)

(9)

(10)

-continued

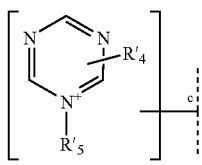

(11)

wherein R'$_4$, which may be identical or different, are chosen from:

linear and branched, saturated and unsaturated, aromatic and non-aromatic, optionally substituted C$_1$-C$_{16}$ hydrocarbon-based chains, which may form at least one 3- to 6-membered carbon-based ring, optionally interrupted with at least one hetero atom or with at least one group bearing at least one hetero atom;

a hydroxyl group, a C$_1$-C$_4$ alkoxy group a C$_2$-C$_4$ (poly)hydroxy-alkoxy group; an alkoxycarbonyl group (RO—CO—) wherein R is chosen from a C$_1$-C$_4$ alkyl radical and an alkylcarbonyloxy radical (RCO—O—) wherein R is chosen from a C$_1$-C$_4$ alkyl radical;

an amino group; an amino group substituted with at least one C$_1$-C$_4$ alkyl radical, which may be identical or different, optionally bearing at least one hydroxyl group, the at least one alkyl radical optionally forming, with the nitrogen atom to which they are attached, a 5- or 6-membered heterocycle optionally bearing another nitrogen or non-nitrogen hetero atom; an alkylcarbonylamino group (RCO—NR'—) wherein R is chosen from a C$_1$-C$_4$ alkyl radical and R' is chosen from a hydrogen atom and a C$_1$-C$_4$ alkyl radical; a carbamoyl group ((R)$_2$N—CO—) wherein R, which may be identical or different, are chosen from a hydrogen atom or a C$_1$-C$_4$ alkyl radical; a ureido group (N(R)$_2$—CO—NR'—) wherein R and R', which may be identical or different, are each chosen from a hydrogen atom and a C$_1$-C$_4$ alkyl radical; a sulfonamide group ((R)$_2$N—SO$_2$—) wherein R, which may be identical or different, are each chosen from a hydrogen atom and a C$_1$-C$_4$ alkyl radical; an alkylsulfonylamino group (RSO$_2$—NR'—) wherein R and R', which may be identical or different, are each chosen from a hydrogen atom and a C$_1$-C$_4$ alkyl radical; a guanidinium group ((R')$_2$N—C(=NH$_2$$^+$)—NR—) wherein R and R', which may be identical or different, are each chosen from a hydrogen atom and a C$_1$-C$_4$ alkyl radical;

a nitro group; a cyano group; a halogen atom;

wherein two radicals R'$_4$ borne by two adjacent carbon atoms of a main ring may optionally form an aromatic or non-aromatic, 5- or 6-membered secondary ring, optionally substituted with at least one group chosen from a hydrogen atom; hydroxyl groups; C$_1$-C$_4$ alkyl radicals; C$_1$-C$_4$ alkoxy radicals; C$_2$-C$_4$(poly) hydroxyalkoxy radicals; amino radicals; amino radicals substituted with at least one C$_1$-C$_4$ alkyl radical, which may be identical or different, optionally bearing at least one hydroxyl group;

$R'_5$ is chosen from linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom; wherein $R'_5$ is such that the atom directly linked to the quaternized nitrogen atom is a carbon atom;

$R'_7$ is chosen from an optionally substituted $C_1$-$C_4$ alkyl radical; an optionally substituted phenyl radical; and an optionally substituted benzyl radical;

the bond c links the cationic radical defined by formulae (1) to (11) to the azo group; wherein said bond may be on the main or secondary ring;

p is an number ranging from 0 to 4, p' is an number ranging from 0 to 2 and p" is an number ranging from 0 to 3;

herein the main ring does not bear the maximum number of substituents, each unsubstituted position bears a nitrogen atom;

LK is chosen from saturated and unsaturated, linear and branched, cyclic and non-cyclic, aromatic and non-aromatic, optionally substituted $C_2$-$C_{40}$ hydrocarbon-based chains, bearing at least one cationic charge, optionally interrupted with at least one hetero atom or group comprising at least one hetero atom;

wherein LK may end with a hetero atom or group bearing at least one hetero atom if LK is linked to $W'_2$ or $W'_5$; and wherein LK may end with a group bearing at least one hetero atom chosen from —CO— and —SO$_2$— if LK is linked to $W_6$ or $W_1$, in contact with the wet or dry fibers for a time that is sufficient to obtain the desired effect.

38. A multi-compartment device comprising at least one compartment comprising a composition comprising, in a medium that is suitable for dyeing keratin fibers, as direct dye, at least one compound of formula (I):

Dye1-LK-Dye2 (I)

or the addition salts thereof with an acid, the electrical neutrality of the compound is ensured by at least one cosmetically acceptable anion An, wherein:

Dye1 and Dye2 are such that the compound of formula (I) is not symmetrical, and are chosen from:

Dye1:

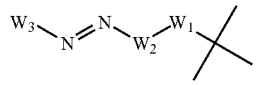 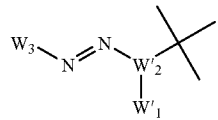

Dye2:

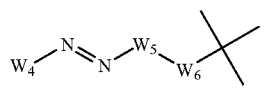 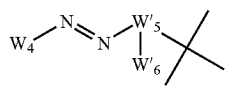

wherein:

$W_1$ and $W_6$, which may be identical or different, are each chosen from —NR$_1$— and —O—, wherein $R_1$ is chosen from a hydrogen atom, and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom;

wherein $R_1$ may form with all or part of the group LK and with the nitrogen atom to which each is attached at least one cationic and non-cationic, saturated and unsaturated, aromatic and non-aromatic, optionally substituted 5- to 7-membered heterocycle;

$W'_1$ and $W'_6$, which may be identical or different, are each chosen from —NR$'_1$R$'_2$ and —OR$'_3$, wherein $R'_1$, $R'_2$ and $R'_3$, which may be identical or different, are each chosen from a hydrogen atom and saturated and unsaturated, aromatic and non-aromatic, optionally substituted $C_1$-$C_{20}$ hydrocarbon-based chains, which may form at least one optionally substituted 3- to 7-membered carbon-based ring, optionally interrupted with at least one hetero atom or with at least one group bearing at least one hetero atom; $R'_1$ and $R'_2$ optionally forming, with the nitrogen atom to which they are attached, an optionally substituted 5- or 7-membered heterocycle optionally comprising another nitrogen or non-nitrogen hetero atom;

wherein $R'_1$, $R'_2$ and $R'_3$, together or separately, may form, with all or part of the group LK and with the nitrogen or oxygen atom to which each is attached, at least one cationic and non-cationic, saturated and unsaturated, aromatic and non-aromatic, optionally substituted 5- to 7-membered heterocycle;

$W_2$, $W_5$, $W'_2$ and $W'_5$, which may be identical or different, are each chosen from:

(a)

(b)

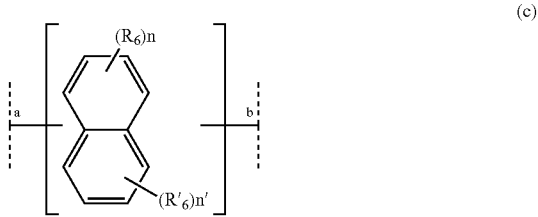

(c)

wherein:

$X_1$ is chosen from a nitrogen atom and CR$_7$;
$X_2$ is chosen from a nitrogen atom and CR$_8$;
$Z_1$ is chosen from a nitrogen atom and CR$_{10}$;
$Z_2$ is chosen from a nitrogen atom and CR$_{11}$;
$R_4$, $R_5$, $R_6$, $R'_6$, $R_7$, $R_8$, $R_{10}$ and $R_{11}$, which may be identical or different, are chosen from:
a hydrogen atom
linear and branched, saturated and unsaturated, aromatic and non-aromatic, optionally substituted $C_1$-$C_{16}$ hydrocarbon-based chains, which may form at least one optionally substituted 3- to 6-membered carbon-based ring, optionally interrupted with at least one hetero atom or with at least one group bearing at least one hetero atom;

a hydroxyl group, a $C_1$-$C_4$ alkoxy group, a $C_2$-$C_4$ (poly)hydroxyalkoxy group; an alkoxycarbonyl group (RO—CO—) wherein R is chosen from a $C_1$-$C_4$ alkyl radical, and an alkylcarbonyloxy radical (RCO—O—) wherein R is chosen from a $C_1$-$C_4$ alkyl radical;

an amino group, an amino group substituted with at least one $C_1$-$C_4$ alkyl radicals, which may be identical or different, optionally bearing at least one hydroxyl group, the at least one alkyl radical optionally forming, with the nitrogen atom to which it is attached, a 5- or 6-membered heterocycle optionally bearing another nitrogen or non-nitrogen hetero atom; an alkylcarbonylamino group (RCO—NR—) wherein R, which may be identical or different, are each chosen from a $C_1$-$C_4$ alkyl radical; a carbamoyl group $((R)_2N—CO)$ wherein R, which may be identical or different, are chosen from a hydrogen atom and a $C_1$-$C_4$ alkyl radical; a ureido group $(N(R)_2—CO—NR'—)$ wherein R and R', which may be identical or different, are each chosen from a hydrogen atom and a $C_1$-$C_4$ alkyl radical; a sulfonamide group $((R)_2N-SO_2—)$ wherein R, which may be identical or different, are each chosen from a hydrogen atom and a $C_1$-$C_4$ alkyl radical; an alkylsulfonylamino group $(RSO_2—NR'—)$ wherein R and R', which may be identical or different, are each chosen from a hydrogen atom and a $C_1$-$C_4$ alkyl radical; a guanidinium group $((R')_2N—C(=NH_2^+)—NR—)$ wherein R and R', which may be identical or different, are each chosen from a hydrogen atom and a $C_1$-$C_4$ alkyl radical;

a nitro group; a cyano group; a halogen atom;

$R_4$, $R_5$, $R_6$, $R'_6$, $R_7$, $R_8$, $R_{10}$ and $R_{11}$, which may be identical or different, may optionally form, with all or some of the groups $W'_1$ or $W'_6$, saturated and unsaturated, aromatic and non-aromatic, optionally substituted 5- to 7-membered heterocycles;

a bond from $W'_2$ to $W'_1$ or to the group LK, or from $W'_5$ to $W'_6$ or to the group LK;

a is the bond from $W_2$, $W_5$, $W'_2$ or $W'_5$ to the azo group —N=N—;

b is the bond from $W_2$ to $W_1$, from $W_5$ to $W_6$, from $W'_2$ to $W'_1$ or to the group LK, or from $W'_5$ to $W'_6$ or to the group LK;

$R_9$ is chosen from:

a hydrogen atom, linear and branched, saturated and unsaturated, aromatic and non-aromatic, optionally substituted $C_1$-$C_{16}$ hydrocarbon-based chains, which may form at least one optionally substituted 3- to 7-membered carbon-based ring, n and n', which may be identical or different, are chosen from integers, wherein their sum is less than or equal to 6;

$W_3$ and $W_4$, which may be identical or different, are each chosen from cationic heteroaromatic radicals chosen from:

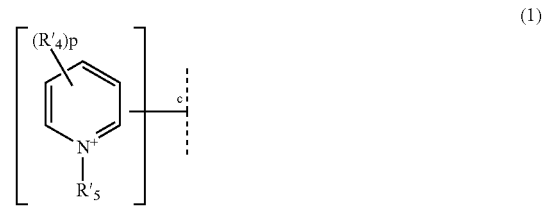

(1)

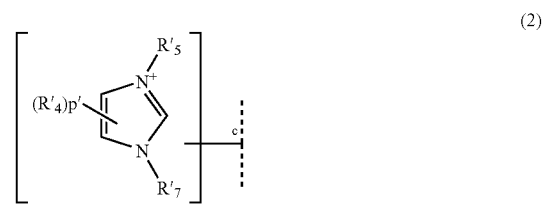

(2)

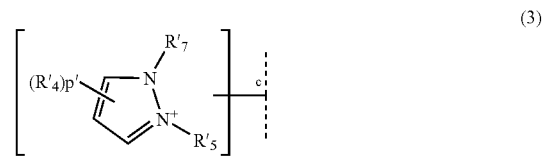

(3)

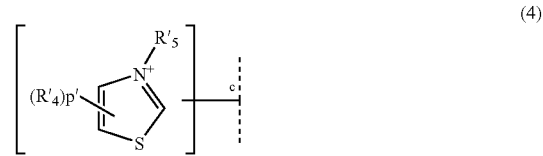

(4)

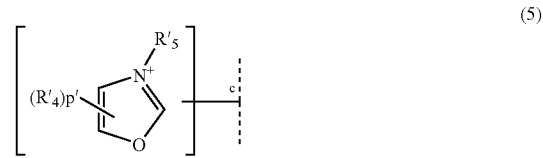

(5)

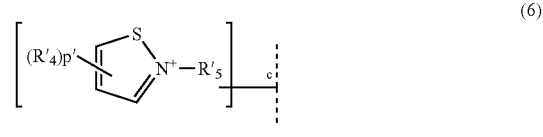

(6)

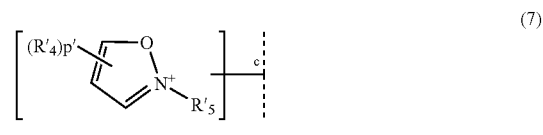

(7)

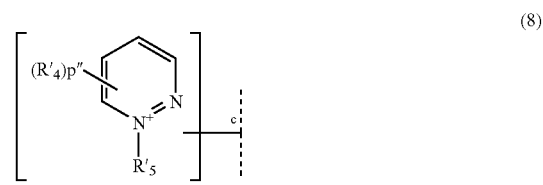

(8)

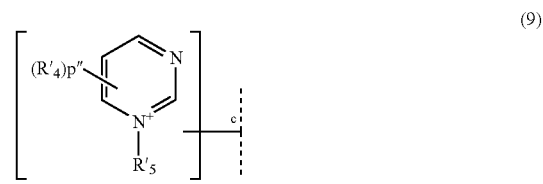

(9)

-continued

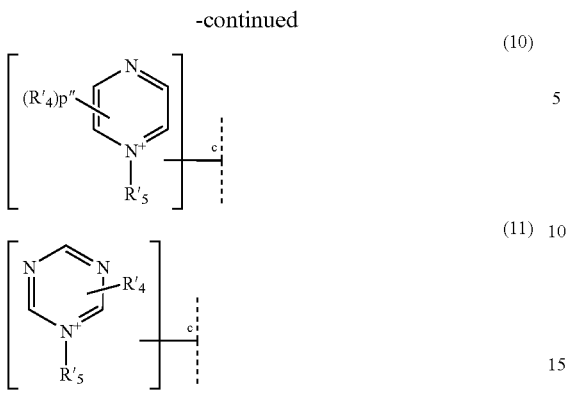

wherein R'$_4$, which may be identical or different, are chosen from:
linear and branched, saturated and unsaturated, aromatic and non-aromatic, optionally substituted C$_1$-C$_{16}$ hydrocarbon-based chains, which may form at least one 3- or 6-membered carbon-based ring, optionally interrupted with at least one hetero atom or with at least one group bearing at least one hetero atom;
a hydroxyl group,
a C$_1$-C$_4$-alkoxy group a C$_2$-C$_4$ (poly)hydroxyalkoxy group; an alkoxycarbonyl group (RO—CO—) wherein R is chosen from a C$_1$-C$_4$ alkyl radical and an alkylcarbonyloxy radical (RCO—O—) wherein R is chosen from a C$_1$-C$_4$ alkyl radical;
an amino group; an amino group substituted with at least one C$_1$-C$_4$ alkyl radical, which may be identical or different, optionally bearing at least one hydroxyl group, the at least one alkyl radical optionally forming, with the nitrogen atom to which they are attached, a 5- or 6-membered heterocycle optionally bearing another nitrogen or non-nitrogen hetero atom; an alkylcarbonylamino group (RCO—NR'—) wherein R is chosen from a C$_1$-C$_4$ alkyl radical and R' is chosen from a hydrogen atom and a C$_1$-C$_4$ alkyl radical; a carbamoyl group ((R)$_2$—N—CO—) wherein R, which may be identical or different, are chosen from a hydrogen atom or a C$_1$-C$_4$ alkyl radical; a ureido group (N(R)$_2$—CO—NR'—) wherein R and R', which may be identical or different, are each chosen from a hydrogen atom and a C$_1$-C$_4$ alkyl radical; a sulfonamide group ((R)$_2$N—SO$_2$—) wherein R, which may be identical or different, are each chosen from a hydrogen atom and a C$_1$-C$_4$ alkyl radical; an alkylsulfonylamino group (RSO$_2$—NR'—) wherein R and R', which may be identical or different, are each chosen from a hydrogen atom and a C$_1$-C$_4$ alkyl radical; a guanidinium group ((R')$_2$N—C(=NH$_2^+$)—NR—) wherein R and R', which may be identical or different, are each chosen from a hydrogen atom and a C$_1$-C$_4$ alkyl radical;
a nitro group; a cyano group; a halogen atom;
wherein two radicals R'$_4$ borne by two adjacent carbon atoms of a main ring may optionally form an aromatic or non-aromatic, 5- or 6-membered secondary ring, optionally substituted with at least one group chosen from a hydrogen atom; hydroxyl groups; C$_1$-C$_4$ alkyl radicals; C$_1$-C$_4$ alkoxy radicals; C$_2$-C$_4$(poly)hydroxyalkoxy radicals; amino radicals; amino radicals substituted with at least one C$_1$-C$_4$ alkyl radical, which may be identical or different, optionally bearing at least one hydroxyl group;

R'$_5$ is chosen from linear and branched, saturated and unsaturated, aromatic and non-aromatic, optionally substituted C$_1$-C$_{16}$ hydrocarbon-based chains, which may form at least one optionally substituted 3- to 6-membered carbon-based ring, optionally interrupted with at least one hetero atom or with at least one group bearing at least one hetero atom; wherein R'$_5$ is such that the atom directly linked to the quaternized nitrogen atom is a carbon atom;

R'$_7$ is chosen from an optionally substituted C$_1$-C$_4$ alkyl radical; an optionally substituted phenyl radical; and an optionally substituted benzyl radical;

the bond c links the cationic radical defined by formulae (1) to (11) to the azo group; wherein said bond may be on the main or secondary ring;

p is an number ranging from 0 to 4, p' is an number ranging from 0 to 2 and p" is an number ranging from 0 to 3;

wherein the main ring does not bear the maximum number of substituents, each unsubstituted position bears a nitrogen atom;

LK is chosen from saturated and unsaturated, linear and branched,-cyclic and non-cyclic, aromatic and non-aromatic, optionally substituted C$_2$-C$_{40}$ hydrocarbon-based chains, bearing at least one cationic charge, optionally interrupted with at least one hetero atom or group comprising at least one hetero atom;

wherein LK may end with a hetero atom or group bearing at least one hetero atom if LK is linked to W'$_2$ or W'$_5$; and wherein LK may end with a group bearing at least one hetero atom chosen from —CO— and —SO$_2$— if LK is linked to W$_6$ or W$_1$, and at least one compartment comprising an oxidizing composition.

* * * * *

UNITED STATES PATENT AND TRADEMARK OFFICE
CERTIFICATE OF CORRECTION

PATENT NO.        : 7,285,138 B2                                             Page 1 of 1
APPLICATION NO.   : 11/159154
DATED             : October 23, 2007
INVENTOR(S)       : Andrew Greaves et al.

It is certified that error appears in the above-identified patent and that said Letters Patent is hereby corrected as shown below:

Claim 29, col. 52, line 45, insert space after "$C_1$-$C_{16}$".

Claim 37, col. 59, line 23, "herein" should read --wherein--.

Signed and Sealed this

Eleventh Day of March, 2008

JON W. DUDAS
*Director of the United States Patent and Trademark Office*